United States Patent [19]

McQuilkin

[11] Patent Number: 5,241,964
[45] Date of Patent: Sep. 7, 1993

[54] NONINVASIVE, NON-OCCLUSIVE METHOD AND APPARATUS WHICH PROVIDES A CONTINUOUS INDICATION OF ARTERIAL PRESSURE AND A BEAT-BY-BEAT CHARACTERIZATION OF THE ARTERIAL SYSTEM

[75] Inventor: Gary L. McQuilkin, New Hope, Minn.

[73] Assignee: Medwave, Incorporated, New Hope, Minn.

[21] Appl. No.: 606,464

[22] Filed: Oct. 31, 1990

[51] Int. Cl.$^5$ .............................................. A61B 5/02
[52] U.S. Cl. .................................... 128/672; 128/691
[58] Field of Search ...................... 128/661.08, 661.09, 128/661.10, 672, 677, 680, 687, 689, 690, 691, 693, 694

[56] References Cited

U.S. PATENT DOCUMENTS

| | | |
|---|---|---|
| 2,658,505 | 11/1953 | Sheer . |
| 2,944,542 | 7/1960 | Barnett . |
| 3,090,377 | 5/1963 | Salisbury . |
| 3,095,872 | 7/1963 | Tolles . |
| 3,157,177 | 10/1974 | Smith . |
| 4,023,563 | 5/1977 | Reynolds . |
| 4,245,648 | 1/1981 | Trimmer . |
| 4,307,727 | 12/1981 | Haynes . |
| 4,349,034 | 9/1982 | Ramsey . |
| 4,425,920 | 1/1984 | Bourland . |
| 4,669,485 | 6/1987 | Russell . |

OTHER PUBLICATIONS

Skidmore, R. and Woodcock, J. P., "Physiological Interpretation of Doppler-shift Waveforms-I, Theoretical Considerations," Ultrasound in Medicine and Biology, vol. 6, pp. 7-10, Pergamon Press Ltd., 1980.
Skidmore, R. and Woodcock, J. P., "Physiological Interpretation of Doppler-shift Waveforms-II, Validation of the Laplace Transform Method for Characterization of the Common Femoral Bloo-Velocity/Time Waveform," Ultrasound in Medicine and Biology, vol. 6, pp. 219-225, Pergamon Press Ltd., 1980.
Skidmore, R., Woodcock, J. P. and Wells, P. N. T., "Physiological Interpretation of Doppler-Shift Waveforms-III, Clinical Results," Ultrasound in Medicine and Biology, vol. 6, pp. 227-231, Pergamon Press Ltd., 1980.
McQuilkin, G., Bourland, J. D., and Geddes, L. A., "Blood Pressure by Pulse Transit Time as an Indicator of Arterial Blood Pressure," Physochophysiology, vol. 18, No. 1, pp. 71-74, 1981.
Geddes, L. A., Voelz, N. H., Babbs, C. F., Bourland, J. D., and Tacker, W. A., "Pulse Transit Time as an Indicator of Arterial Blood Pressure", Psychophysiology, vol. 18, No. 1, pp. 71-74, 1981.
Toy, S. M., Melbin, J., and Noordergraaf, A., "Reduced Models of Arterial Systems," IEEE Transactions on Biomedical Engineering, vol. BME-32, No. 2, pp. 174-176, Feb. 1985.
Cui, T., Li, J. K-J., and Drzwekiecki, G., "Evaluation of an Arterial System Model Incorporating Nonlinear Compliance," Proceedings of the Ninth Annual Conference of the IEEE Engineering in Medicine and Biology Society, pp. 1477-1478, vol. 8, 1987.
Bergel, D. H., "The Dynamic Elastic Properties of the Arterial Wall", Journal of Physiology, 156:458-469, 1961.

(List continued on next page.)

Primary Examiner—Lee S. Cohen
Assistant Examiner—J. P. Lacyk
Attorney, Agent, or Firm—Kinney & Lange

[57] ABSTRACT

A noninvasive arterial pressure monitor provides calibrated, continuous pressure waveform and beat-by-beat pressure values with no occlusion of an artery during an extended monitoring period. Noninvasive doppler sensors are secured over a major artery. Signals from the sensors are used to mathematically characterize the artery. The time-varying arterial resonant frequency is correlated to blood pressure throughout the cardiac cycle. Doppler sensors provide bi-directional flow velocity waveforms from which arterial resonant frequency may be calculated. A calibration cuff is used infrequently to calibrate the system to units of pressure.

68 Claims, 21 Drawing Sheets

OTHER PUBLICATIONS

Bramwell, J. C., Downing, A. C., and Hill, A. V., "The Effect of Blood Pressure on the Extensibility of the Human Artery," Heart, 10:289–300, 1923.

Busse, R., Bauer, R. D., Schabert, A., Summa, Y., Bumm, P., and Wetterer, E., "The Mechanical Properties of Exposed Human Common Carotid Arteries in Vivo," Basic Research in Cardiology, 74:545–554, Sep.-Oct., 1979.

Carter, Stefan A., "Effect of Age, Cardiovascular Disease, and Vasomotor Changes on Transmission of Arterial Pressure Waves Through the Lower Extremities," Angiology, 29(8) 601–616, Aug., 1978.

Gribbin, Brian, Steptoe, Andrew, and Sleight, P., "Pulse Wave Velocity as a Measure of Blood Pressure Change", Psychophysiology, 13:86–90, Jan. 1976.

Laogun, A. A., Newman, D. L., and Gosling, R. G., "Comparison of Pulse Wave Velocity Measured by Doppler Shifted Ultrasound and Electromagnetic Flowmetry,". Ultrasound in Medicine and Biology, 3:367–371, 1978.

McQuilkin et al.; Blood Pressure by Pulse Transit Time; *Medical Electronics*, pp. 68–69; Jun. 1980.

TARGET A1=1.000000, A2=1.000000, TAU=0.155555, ZETA=0.400000, $F_n$=3.500000
BST    A1=0.995797, A2=0.995797, TAU=0.151494, ZETA=0.394417, $F_n$=3.497091
TARGET P1=1.000000, p2=6.666667, P3=20.155204, P4=0.796452
BST    P1=0.991612, P2=6.600919, P3=20.196162, P4=0.669459
ITERATIONS=1000, ERROR=0.000015, COEF=(0.200000, 3.000000, 3.000000, 3.000000)

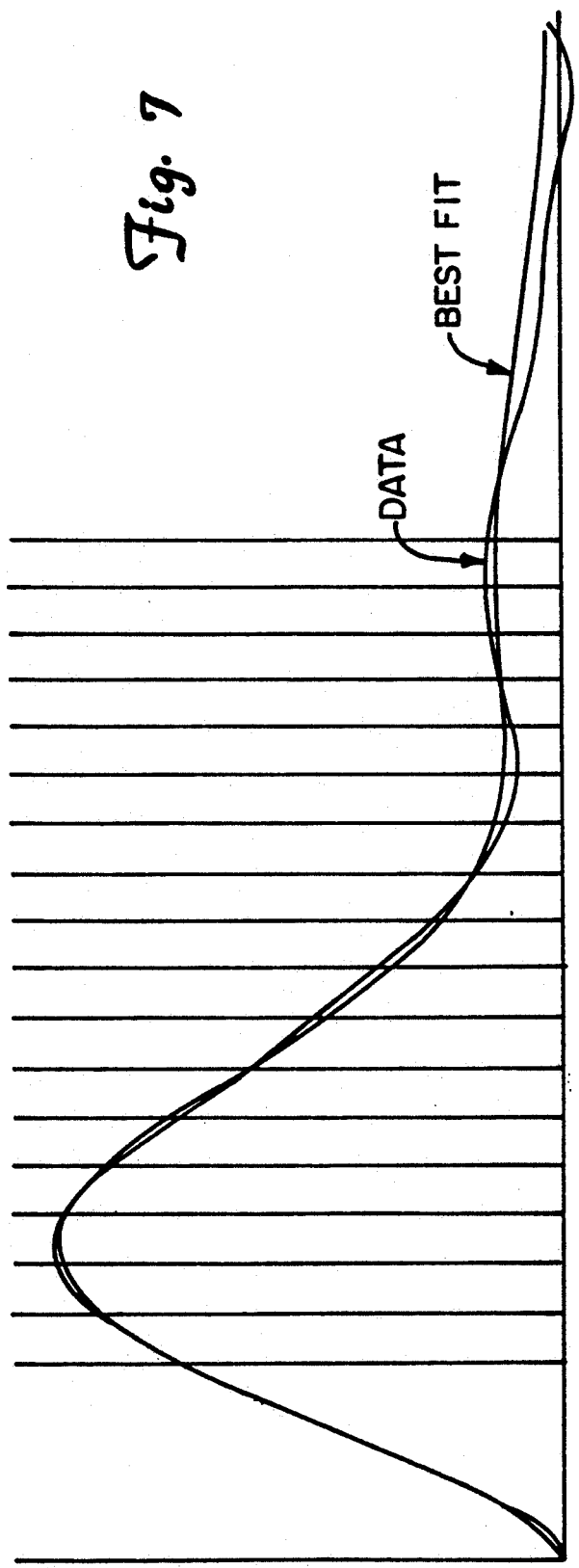

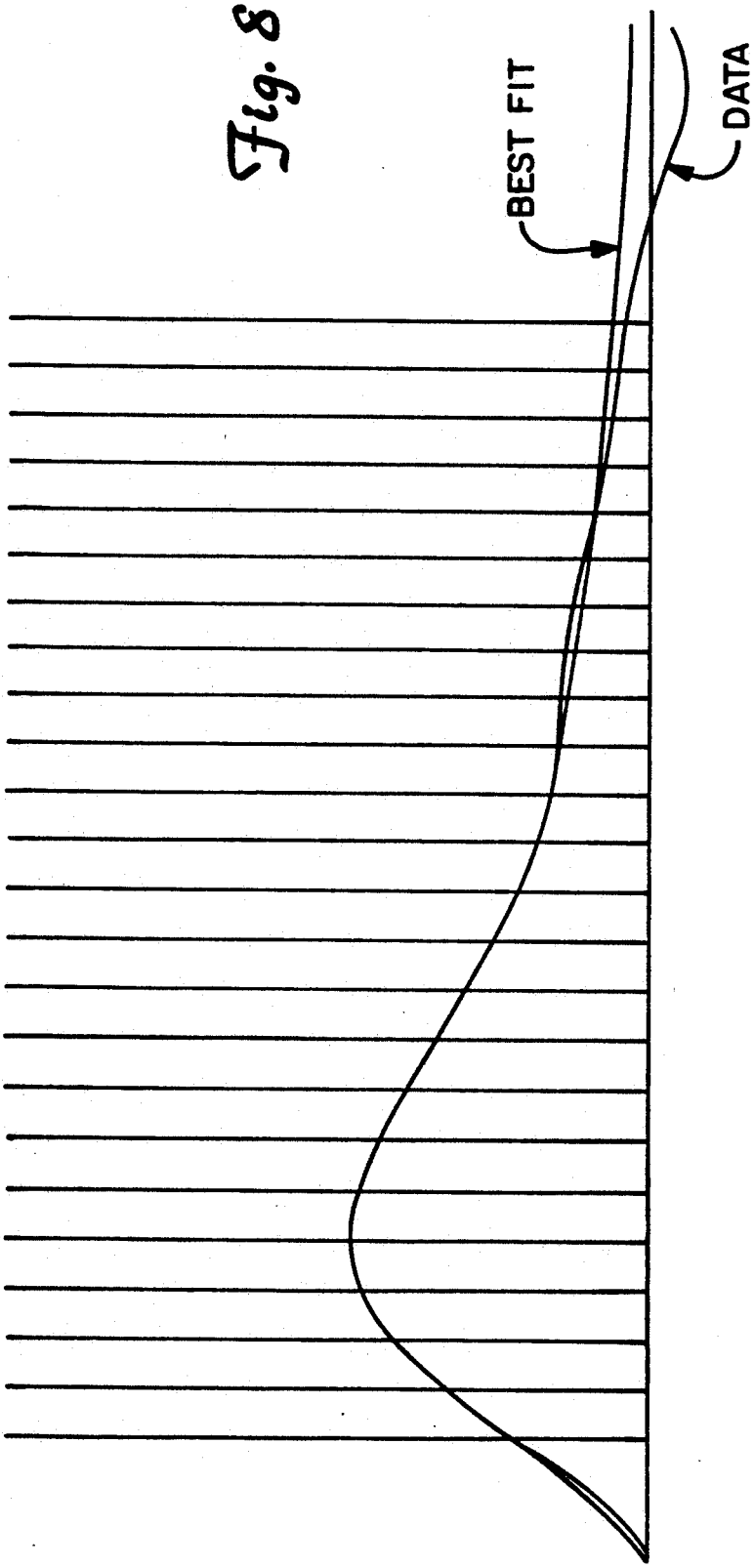

NONINVASIVE, NON-OCCLUSIVE METHOD AND APPARATUS WHICH PROVIDES A CONTINUOUS INDICATION OF ARTERIAL PRESSURE AND A BEAT-BY-BEAT CHARACTERIZATION OF THE ARTERIAL SYSTEM

BACKGROUND OF THE INVENTION

The present invention relates to measuring arterial pressure. In particular, the present invention relates to a mathematical characterization of the arterial system to obtain time-varying parameters which are highly correlated with arterial pressure.

Current methods used to measure arterial pressure may be classified as either invasive or noninvasive. Invasive techniques employ a surgical procedure in which a catheter is introduced into the lumen of the artery. Pressure within the artery or within the catheter is measured directly with a pressure transducer. Noninvasive techniques commonly employ the inflation and deflation of an occlusive cuff. Such cuff-based systems provide an intermittent indication of systolic (maximum or peak), mean (time average), or diastolic (minimum) pressure values.

I. INVASIVE TECHNIQUES

Invasive techniques for measuring arterial pressure, referred to as arterial lines, may use either a fluid-filled catheter system or a catheter-tip pressure transducer. While both invasive systems have the potential for accurate, continuous measurement of arterial pressure, they also possess negative traits. Both require the attention of a physician to insert them. Even without any complications, this procedure may take in excess of 15 minutes. Maintenance of the arterial line requires the constant surveillance by skilled clinicians to avoid mishap. While frequently used without incident, complications may include thrombosis of the artery, air emboli, thromboembolism, bacteremia, or hematoma upon withdrawal of the catheter. Immediately following removal of the catheter, firm pressure must be maintained for at least 10 minutes. Sandbags are sometimes applied for 1-2 hours on femoral sites.

(1) Fluid-Filled Catheter System

The fluid-filled catheter system is the most commonly used of the invasive methods. While exhibiting the traits common to both invasive techniques, this system also employs a clutter of equipment. A disposable pressure transducer, a fluid-filled catheter partially inserted into the artery, tubing, stopcocks, flow valves, and a pressurized bag of heparinized saline are required. Measurement accuracy can be compromised by bubbles or blood clots within the catheter system. Excessive catheter length and/or insufficient stiffness of the catheter wall creates a catheter resonance within the bandwidth of the pressure waveform. Consequently, such a resonance yields an overestimation of the systolic pressure.

(2) Catheter-Tip Pressure Transducer

The catheter-tip pressure transducer system eliminates the inaccuracies of catheter resonance by locating a miniaturized pressure transducer on the very tip of the catheter. However, blood clots over the catheter tip continue to result in significant waveform distortion. The risk factors common to all invasive systems still apply. Since the cost of the disposable, catheter-tip transducer is an order of magnitude higher than its fluid-filled counterpart, it is seldom selected for routine use.

II. NONINVASIVE TECHNIQUES

Noninvasive techniques for measuring arterial pressure include an assortment of technologies and applications. Intermittent methods employ the inflation and deflation of an occlusive cuff. Systolic, mean, or diastolic pressure is identified as the cuff pressure occurring simultaneously with a specific arterial or cuff event. Indications of arterial pressure on a beat-by-beat basis have been attempted via application of pulse-wave velocity. The propagation of a specific, temporal, characteristic of the pressure waveform has been found to track diastolic pressure. In the prior art, the continuous pressure waveform has been obtained via noninvasive means with only marginal success. In comparison to invasive methods, all noninvasive techniques significantly reduce patient risk. In addition, the time required to set up, maintain, and remove the equipment is substantially less with noninvasive devices.

(1) Intermittent Methods

Intermittent methods for obtaining a noninvasive indication of arterial pressure generally use an occlusive cuff around the upper arm. The cuff is inflated to a pressure above systolic pressure and then deflated at a rate of 2-4 mmHg per heart beat. The cuff pressures occurring simultaneously with specific events within the arterial or cuff systems are used to assign values to systolic, mean, or diastolic pressures. The following methods are known:

a) Palpatory Method

In the palpatory method, the clinician places his or her fingers over the radial artery distal to the occlusive cuff. As the cuff pressure is decreased from a value greater than systolic pressure, the first radial pulse felt by the clinician identifies the simultaneously occurring cuff pressure as systolic pressure. Mean and diastolic pressures cannot be accurately determined with this method.

b) Flush Method

With the flush method, blood is driven from the arm by the application of pressure. This blanching is conducted prior to the inflation of the occlusive cuff. The cuff is then inflated to a pressure above systolic pressure while the blood supply in the arm is reduced. After removing the blanching force, the cuff pressure is slowly decreased. Systolic pressure is identified as the cuff pressure occurring simultaneously with the transition of arm color from white to pink. Mean and diastolic pressures cannot be obtained in this manner.

c) Auscultatory Method (Korotkoff/Riva Rocci)

Auscultation is the act of listening to sounds arising within the body for the purpose of diagnostics or treatment. The auscultatory method for measuring blood pressure (also known as the Korotkoff and Riva Rocci methods), commonly employed in hospitals and clinics, involves listening to Korotkoff sounds emanating from the brachial artery distal to an occlusive cuff placed on the upper arm. A stethoscope, is typically used to amplify these sounds while the cuff proximal to the brachial site is deflated from a pressure greater than systolic pressure to a pressure less than diastolic pressure. The appearance, intensity, and disappearance of the Korotkoff sounds (named in honor of the Russian physician who initially attempted this method in 1905) are used in conjunction with the simultaneous cuff pressure to yield a noninvasive indication of systolic and diastolic pressures.

With the auscultatory method, initially, the occlusive cuff is rapidly inflated to a pressure estimated to be above the systolic pressure of the artery. The observer listens for the ensuing Korotkoff sounds as the cuff is slowly deflated (2–4 mmHg per heart beat). The cuff pressure occurring simultaneously with the onset of Korotkoff sounds is taken as systolic pressure. As cuff pressure continues to fall, the sound intensity increases, then decreases, then increases again with a thumping or snapping quality, which shortly becomes muffled and disappears. The cuff pressure associated with the timing of the muffling or disappearance of the Korotkoff sound is taken as diastolic pressure. Since the cuff pressures at which the muffling and disappearance of sounds occur are substantially different in some patients, many clinicians regard the muffling pressure as diastolic. To minimize the uncertainty associated with the identification of diastolic pressure, some institutions require that both muffling and disappearance pressures be recorded for the 'diastolic' measurement.

While this method is reasonably simple to employ and is universally used to measure blood pressure, its accuracy is largely dependent upon the care and skill of the clinician making the measurement. An excessively fast cuff deflation rate may significantly underestimate true pressures. Two clinicians observing the same patient may report different pressures due to differences in their hearing acuity and their ability to identify the appearance, muffling, and disappearance of the Korotkoff sounds. Application of an inappropriately-sized cuff results in additional measurement error. In the typical clinical environment, Bruner reported a correlation coefficients of 0.64 between auscultatory systolic pressure and direct systolic pressure. Similarly, the correlation coefficient for diastolic pressures was 0.60.

d) Oscillometric Method

The oscillometric method for measuring arterial pressure employs the observation of amplified cuff oscillations as cuff pressure is slowly decreased (2-4 mmHg per heart beat) from a value greater than systolic pressure to a value less than diastolic pressure. The maximum amplitude of cuff oscillations occurs when the decreasing cuff pressure is equal to mean arterial pressure. Geddes reported that systolic and diastolic pressures may also be inferred from the amplitude of cuff oscillations but with less accuracy.

e) Ultrasonic Wall-Motion Method

Characteristic motion of the arterial wall beneath an occlusive cuff has been shown by investigators to be an accurate indicator of systolic and diastolic pressures. The occlusive cuff is inflated to a pressure in excess of systolic pressure and slowly deflated (2-4 mmHg per heart beat). As the cuff pressure passes systolic and diastolic pressure, characteristic motions are observable in the arterial wall via ultrasonic doppler sensors located under the cuff.

While this method has an apparent accuracy advantage over some other methods, the reliance upon the cuff and wall motion sensors makes it highly susceptible to motion artifacts. The doppler wall motion frequency content is identical to that of undesired arm motion. Therefore electronic filtering to separate the wall and arm motion becomes extremely difficult.

f) Automatic Intermittent Methods

With low cost microprocessors and electronic controls available, numerous automated systems have appeared. While the displays and controls may vary, it is important to recognize that all employ one of the basic techniques described above. Since the oscillometric method requires only a cuff, it is a prime choice for automated systems.

(g) Pulse-Wave Velocity

Pulse-wave velocity (PWV), the speed with which a pressure wave propagates along an artery has been shown to track arterial pressure. With this method, a temporal characteristic of the pressure (or flow) waveform is observed at two arterial sites located different distances from the heart. The time delay between a specific waveform characteristic appearing at each site as the waveform propagates along the vessel is typically used together with the distance between sites to provide a velocity computation.

The most common method of computing PWV, herein referred to as the "foot-to-foot" method, uses the onset of the systolic upstroke as the reference characteristic. This approach has some significant deficiencies. First, such a computation of beat-to-beat PWV, at best, provides only one measurement with each cardiac cycle. Diastolic pressure has been found to highly correlate with foot-to-foot PWV. Therefore, this method provides only diastolic pressure. Systolic and mean pressure values are not provided. In addition, the exact onset of the rapid upstroke, or foot of the waveform, is not easily identified with sufficient timing resolution using common threshold techniques. This is due to the fact that the foot of the waveform is the summation of numerous harmonic frequency components varying in both amplitude and phase. Since the artery is a dispersive system, the propagation velocity of each harmonic component is a function of its frequency. Work done in conjunction with the present invention shows that the arterial frequency response changes with pressure, providing a very complex relationship between the frequency components making up any temporal waveform characteristic.

Attempts by some researchers to use the QRS complex of an electrocardiogram (ECG) as the initial timing reference for the computation of PWV adds a further source of error to the measurement. The isovolumic contraction period, that time required for the heart to convert the electrical stimulus into a productive mechanical contraction capable of ejecting blood from the ventricles, is added to the propagation delay used to compute PWV. This period has been shown to be uncorrelated with arterial pressure and may make up a substantial part of the ECG-peripheral pulse delay. Therefore, the use of the QRS-peripheral pulse method further degrades any potential correlation between beat-to-beat PWV and arterial pressure.

(2) Continuous Methods

Current methods for continuously monitoring arterial pressure attempt to provide a calibrated pressure waveform. To date none have gained wide clinical acceptance.

a) Finger Cuff Technique

One device utilizes a partially inflated finger cuff, an infrared finger sensor, and a servo system to control the finger cuff pressure. This system attempts to maintain a constant arterial diameter in the monitored finger by adjusting the finger cuff pressure. The infrared sensor provides the estimate of arterial diameter. A continuous pressure waveform is its output.

This system has several potential disadvantages. Because it uses a partially inflated cuff, it is extremely sensitive to motion artifacts. The partially inflated cuff occludes arterial flow. Since venous and capillary pressures are substantially lower than arterial pressure, the venous and capillary flows are compromised in the monitored finger. The extremely peripheral measurement site raises questions about accuracy during shock and other conditions accompanied by circulatory shutdown.

b) Partially Inflated Cuff

Another system relies on a partially inflated cuff as the sensor. This device inflates the cuff, placed on the upper arm, to approximately 20 mmHg. Oscillations in cuff pressure generated by the arterial pulse are monitored.

This device appears to have numerous deficiencies. As is evident from the oscillometric method, the maximum energy transfer from artery to cuff occurs when the cuff pressure is equal to the mean arterial pressure. This energy transfer is greatly reduced at pressures significantly below diastolic pressure. Cuff oscillation were approximately 1 mmHg peak-to-peak with a strong pulse. Minor motion artifacts may be many times greater than this amplitude. Even the cuff pressure of 20 mmHg is sufficient to compromise venous and capillary pressure during an extended monitoring period. Physiologically, pulse pressure and mean pressure do not necessarily track.

c) General Tonometry

Tonometry, in general, employs a means of applying a pressure transducer against the exterior wall of the artery in an attempt to measure the pressure within the vessel.

Several difficulties exist for this general technique. The characteristics of the tissue between the skin and the arterial wall add an indeterminate term in the calibration equation. The stiffness of the arterial wall itself adds another uncertainty. The positioning of the pressure sensor is critical. Any motion, whatsoever, is likely to cause gross fluctuations.

d) Tonometry with a Partially-Collapsed Arterial Wall

One device attempts to remedy some of the shortcomings of generalized tonometry. Such a device employs a sophisticated electro-mechanical sensor to locate the artery. It attempts to minimize the loss of accuracy due to the arterial wall stiffness by partially collapsing the wall during the extended measurement period. In order to maintain the collapsed arterial wall, this device continuously applies a "hold down" pressure approximately equal to mean arterial pressure. The device automatically recalibrates the system every 2-5 minutes with a fully-occlusive arm cuff.

While this system employs a very sophisticated sensor, it is still plagued by several serious shortcomings. From a clinical vantage point, its function is little different than an automated cuff system set for a repetition interval of 2-5 minutes. The patient discomfort of multiple inflations is identical. Maintaining the arterial wall in a partially-collapsed, unstable state is another difficulty. The calibration remains accurate for only a narrow pressure range around the hold down pressure. If arterial mean pressure changes from the pre-set hold down pressure gross nonlinearities are encountered, thus the need for frequent recalibrations. Since the hold down pressure exceeds venous and capillary pressures, vessel occlusion may seriously limit its application to extended monitoring. As with any tonometry system, motion artifacts are severe and limit use to only very still patients.

SUMMARY OF THE INVENTION

The present invention is a noninvasive, arterial pressure monitor which provides calibrated, continuous pressure waveforms and beat-by-beat pressure values with no occlusion of the artery during an extended monitoring period. One or more noninvasive sensors are secured over a major artery. Signals from these sensors exhibit attributes of the underlying artery. Parameters, which characterize the artery, are extracted from these sensor signals via signal processing techniques. One of these parameters, the time-varying, arterial resonant frequency, is highly correlated to the time-varying pressure within the artery. Therefore, tracking the time-varying resonant frequency of the vessel provides a highly correlated, time-varying, indication of arterial pressure. By utilizing the resonant frequency parameter, in conjunction with the other arterial parameters, the entire arterial pressure waveshape may be regenerated, calibrated, and displayed.

This invention employs the artery itself as the pressure transducer. The pressure-sensitive arterial resonant frequency, is determined largely by the characteristics of the aorta and major arterial branches. This characteristic is tracked on a beat-by-beat basis and within each cardiac cycle. This time-varying, resonant frequency has been found to be linearly proportional to the time-varying pressure within the artery over a wide range of pressures.

The sensors acquire physiological signals from sites on the artery. Typically, a proximal sensor is located over the brachial artery of the arm and a distal sensor is located over the ulnar or radial artery. Presently, continuous-wave, bi-directional, doppler sensors provide acceptable quality signals. The sensors signals, after appropriate doppler signal detection, provide bi-directional, flow velocity waveforms which exhibit the desired arterial resonant frequency, damping characteristic, and systemic decay time constant.

The sensor signals are processed by a series of stages to extract the desired arterial information. A preprocessing stage filters, identifies, aligns, and averages the signals associated with each cardiac cycle. Next, a parameter-estimation processing stage uses these signals to track temporal changes in the resonant frequency, damping coefficient, decay time constant and offset parameters common to both the arterial segment and a mathematical flow model of the arterial system. These arterial parameters are then used to generate a pressure waveform having the units of resonant frequency.

The calibration of resonant frequency, in Hertz (Hz), to pressure, in millimeters of mercury (mmHg), is accomplished by the inflation and deflation of a noninvasive cuff placed on the upper arm. The doppler flow sensor distal to the cuff provide improved pressure accuracy over many automated cuff systems. Once a single cuff cycle has calibrated the pressure waveform, the system remains calibrated throughout an extended monitoring period without further occlusive interruption.

The output from this invention may be in the form of a digital display of systolic, mean, and diastolic pressure values or the display of the entire calibrated pressure waveform on devices such as cathode-ray tube or liquid crystal displays. The calibrated pressure waveform can be used to electronically replicate the standard, direct pressure transducer. This electronic replacement for the mechanical sensor enables the transfer of the calculated pressure waveform to direct pressure monitors and associated central monitoring stations common in intensive care units.

BRIEF DESCRIPTION OF THE DRAWINGS

FIG. 7 shows flow velocity data from a proximal sensor and a fit to a mathematical curve.

FIG. 8 shows flow velocity from a distal sensor and fit to a mathematical curve.

DETAILED DESCRIPTION OF THE PREFERRED EMBODIMENTS

I. Overview

Figure 1A:
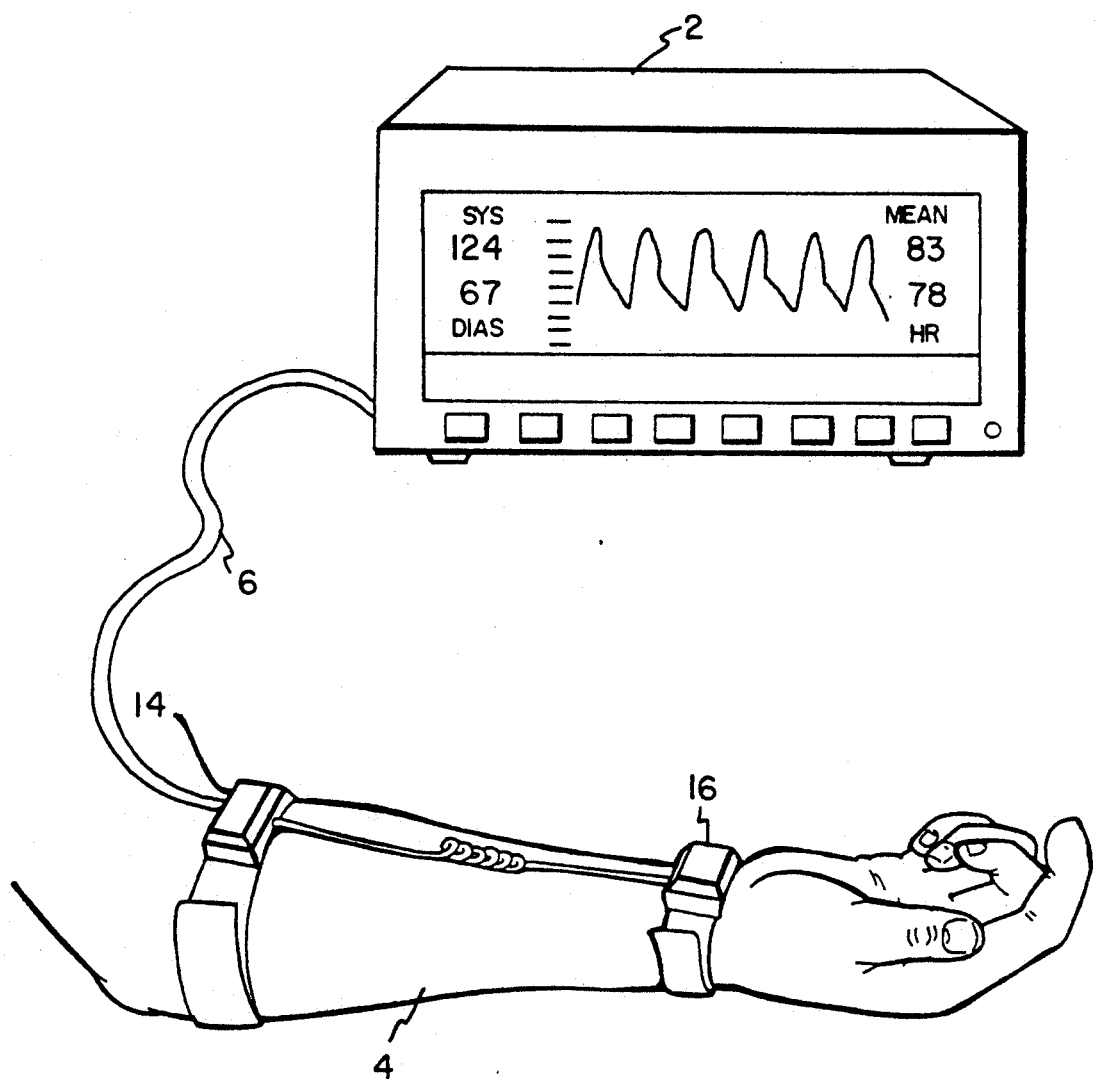
FIG. 1A is diagram of the present invention.

FIG. 1A shows a monitor 2 in accordance with the present invention coupled to an arm 4 of a patient. A cord 6 couples monitor 2 to sensors 14 and 16 which are positioned over brachial and ulnar arteries in arm 4. Monitor 2 displays the calculated pressure waveform in arm 4.

Figure 1B:
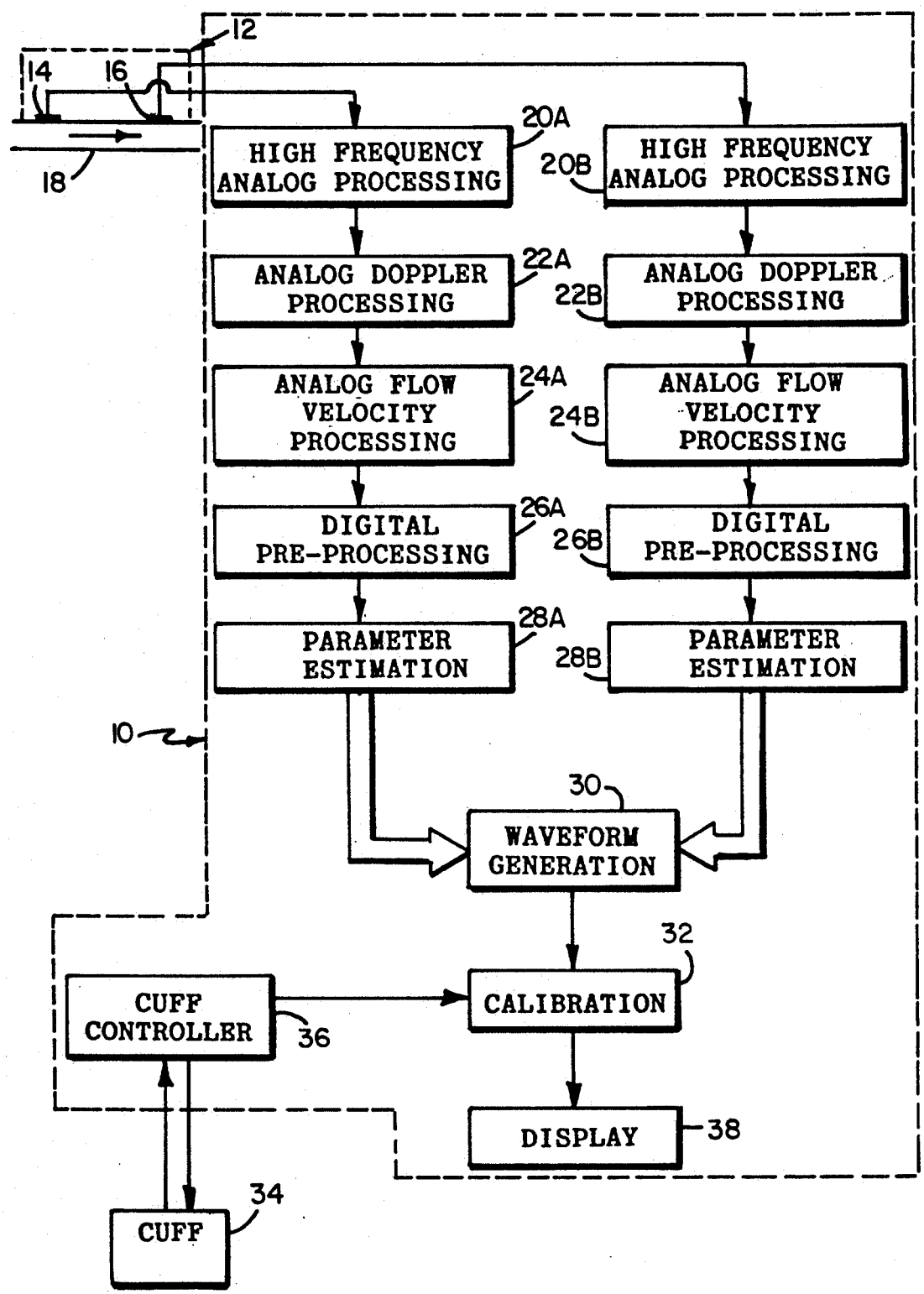
FIG. 1B is a block diagram of the arterial pressure measurement apparatus of the present invention.

FIG. 1B shows a block diagram 10 of a blood pressure monitor 2 in accordance with the present invention. Blood pressure monitor 2 includes a sensor unit 12. Sensor unit 12 includes a proximal doppler sensor 14 and a distal doppler sensor 16 which sense blood flow in an artery 18. Sensors 14 and 16 are connected to high frequency analog processing circuits 20A and 20B, respectfully. High frequency analog processing circuits 20A and 20B provide outputs which are connected to analog doppler processing circuits 22A and 22B. Analog doppler processing circuits 22A and 22B are connected to analog flow velocity processing circuits 24A and 24B. Digital preprocessing circuits 26A and 26B receive inputs from analog flow velocity processing circuits 24A and 24B. Outputs of digital preprocessing circuits 26A and 26B are connected to parameter estimation circuits 28A and 28B. A waveform generation circuit 30 receives inputs from parameter estimation circuits 28A and 28B. These two inputs are combined by waveform generation circuit 30, which provides an input to calibration circuit 32. Calibration circuit 32 also receives an input from a cuff 34 through a cuff controller 36. Calibration circuit 32 provides an input to display 34.

Sensor unit 12 provides sensor outputs for proximal sensor 14 and distal sensor 16. Processing stages 20A through 26A and 20B through 26B provide preprocessing stages which filter, identify, align, and average signals associated with each cardiac cycle. Parameter estimation circuits 28A and 28B use these signals to track temporal changes in the resonant frequency, damping co-efficient, decay time constant, and offset parameters. These parameters are then used by waveform generator 30 to generate a pressure waveform having the units of resonant frequency. The resonant frequency output of waveform generator 30 is calibrated from units of Hertz to units of pressure by calibration stage 32. Calibration stage 32 uses information from cuff 34 and processing cuff controller 36 to accurately calibrate the output of waveform generation circuit 30 to pressure. Once a single cuff cycle has calibrated the pressure waveform, the system remains calibrated throughout an extended monitoring period. Display 38 provides the calibrated pressure waveform and a digital display of the systolic mean and diastolic pressure values.

The operation of blood pressure monitor 10 is described below in more detail.

II. Theory of the Invention

The present invention is based upon a theoretical model which describes the arterial system in terms of a flow output from the aorta, a vascular segment extending from the aorta to a distal site, a peripheral flow waveform, and peripheral impedance. Within this model the arterial segment is represented as a transfer function or filter which has the aortic flow as its input and the distal flow as its output. Mathematically, the artery is represented as a second-order resonant system with the resonant frequency instantaneously modulated by the arterial pressure within the vessel.

III. Flow Model of the Arterial System

Figure 2:
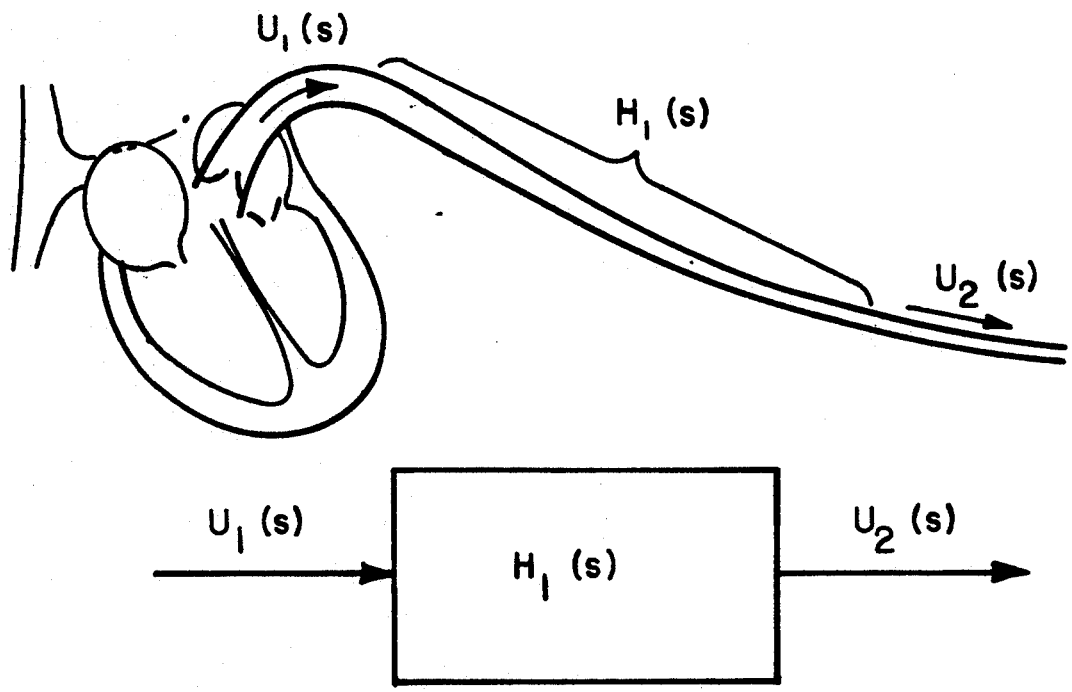
FIG. 2 is a block diagram of an arterial flow model.

FIG. 2 is a model of arterial flow at a peripheral site. The flow out of the aorta is represented in FIG. 2 by $U_1(s)$. This flow is filtered by the elastic properties of the arterial segment located between the aorta and the peripheral site of interest. $U_2(s)$ is represented as:

$$U_2(s) = U_1(s) \cdot H_1(s) \qquad \text{Equation 1}$$

Figure 3:
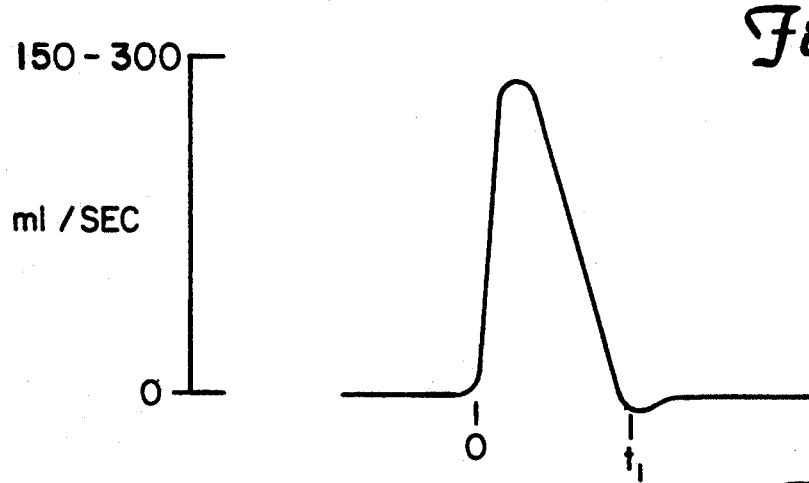
FIG. 3 is a waveform of a typical aortic flow.

Aortic flow is similar to that shown in FIG. 3. The width, $t_1$, varies from 0.17 seconds to 0.35 seconds.

Since flow q is equivalent to the product of flow velocity u and cross-sectional area A flow velocity may be used as an accurate indicator of flow for constant or nearly constant vascular diameter.

Flow = Flow Velocity × Cross-sectional area  Equation 2

$$q = u \times A = u \times \pi d^2/4 \quad \text{Equation 3}$$

For example, a pulse pressure of 37 mmHg has resulted in a ±4% change in canine aortic diameter. This results in a change in aortic cross-sectional area of ±8%. The less elastic peripheral vessels are expected to exhibit less variation in cross-sectional area. Minor changes in arterial diameter do not materially affect model performance since the parameters of major interest are minimally related to amplitude of the flow or flow velocity. Cross-sectional area is, therefore, considered constant in this model.

$$q = u \times A \quad \text{Equation 4}$$

where A is a constant.

Figure 4:
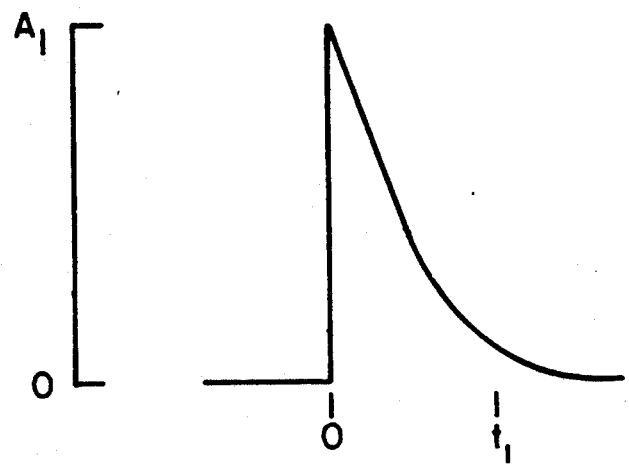
FIG. 4 is a mathematical model of aortic flow velocity.

In this model aortic flow and flow velocity, $U_1(s)$, is represented by a decaying exponential as shown in FIG. 4. Further refinements to this model include a representation of the aortic waveform with a second or third order function.

$$u_1(t) = A_1 e^{-t/\tau} \quad \text{Equation 5}$$

The Laplace transform of $u_1(t)$ is:

$$L\{u_1(t)\} = A_1 \left[ \frac{1}{s + \frac{1}{\tau}} \right] \quad \text{Equation 6}$$

The flow velocity waveform can be fitted by a third order mathematical model. Based on this information and the decaying exponential shape of aortic flow, the arterial transfer function suggests a second order mathematical model. Therefore, $$H_1(s) = \frac{A_2 \omega_n^2}{s^2 + 2\zeta\omega_n s + \omega_n^2} \quad \text{Equation 7}$$

with $\omega_n$ the natural resonant frequency of the vascular segment between the aorta and the peripheral site of interest; $\zeta$, is the damping coefficient indicative of proximal vascular occlusion and $A_2$ is a scaler.

Combining Equations 1, 6 and 7 results in:

$$U_2(s) = \left[ \frac{A_1}{s + \frac{1}{\tau}} \right] \left[ \frac{A_2 \omega_n^2}{s^2 + 2\zeta\omega_n s + \omega_n^2} \right] \quad \text{Equation 8}$$

With "a" substituted for $1/\tau$, the partial fractions expansion of equation may be written as:

$$U_2(s) = \left[ \frac{K_1}{s + a} \right] + \left[ \frac{K_2 s + K_3}{s^2 + 2\zeta\omega_n s + \omega_n^2} \right] \quad \text{Equation 9}$$

with:

$$K_1 = \left[ \frac{A_1 A_2 \omega_n^2}{a^2 - 2\zeta\omega_n a + \omega_n^2} \right] \quad \text{Equation 10}$$

$$K_2 = -K_1 \quad \text{Equation 11}$$

$$K_3 = K_1(a - 2\zeta\omega_n) \quad \text{Equation 12}$$

With appropriate algebraic manipulation, Equations 9 through 12 may be rewritten in the following form convenient for transformation to the time domain:

$$U_2(s) = \frac{K_1}{s+a} + K_2 \left[ \frac{s + \zeta\omega_n}{(s+\zeta\omega_n)^2 + \omega_n^2(1-\zeta^2)} \right] + $$
$$K_2(\zeta\omega_n - a) \left[ \frac{1}{(s+\zeta\omega_n)^2 + \omega_n^2(1-\zeta^2)} \right] \quad \text{Equation 13}$$

Applying the inverse Laplace transform, Equation 13 may be converted to the following time domain expression:

$$u_2(t) = K_1 e^{-at} + K_2 [e^{-\zeta\omega_n t} \cos(\omega_n \sqrt{1-\zeta^2})t] + $$
$$K_2(\zeta\omega_n - a) \left[ \frac{1}{\omega_n \sqrt{1-\zeta^2}} \right] [e^{-\zeta\omega_n t} \sin \omega_n \sqrt{1-\zeta^2}\ t] \quad \text{Equation 14}$$

Substituting expressions 10, 11, and 12 into Equation 14 and regrouping terms yields:

$$u_2(t) = \left[ \frac{A_1 A_2 \omega_n^2}{a^2 - 2\zeta\omega_n a + \omega_n^2} \right] e^{-at} - $$
$$\left[ \frac{A_1 A_2 \omega_n^2}{a^2 - 2\zeta\omega_n a + \omega_n^2} \right] e^{-\zeta\omega_n t} \left[ \cos\omega_d t + \left( \frac{\zeta\omega_n - a}{\omega_d} \right) \sin\omega_d t \right] \quad \text{Equation 15}$$

Variable substitutions in Equation 15 are:

$$a = \frac{1}{\tau} \quad \text{and} \quad \omega_d = \omega_n \sqrt{1-\zeta^2} \quad \text{Equation 16}$$

Figure 5A:
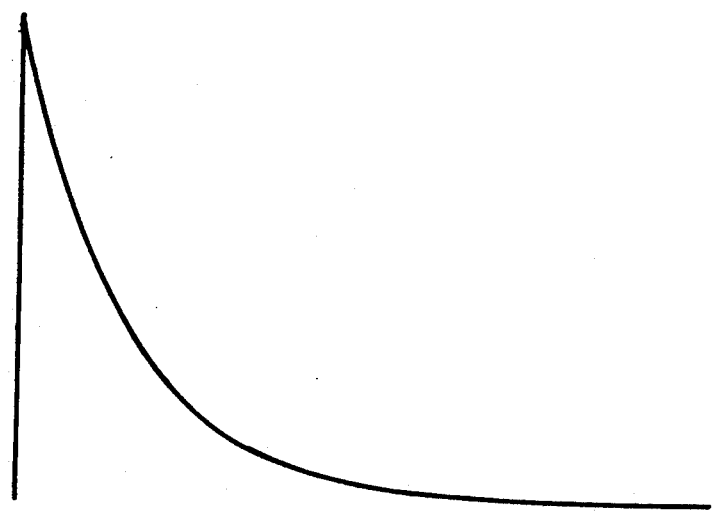
FIG. 5A is a graph of a first order term present in peripheral flow waveform.
Figure 5B:
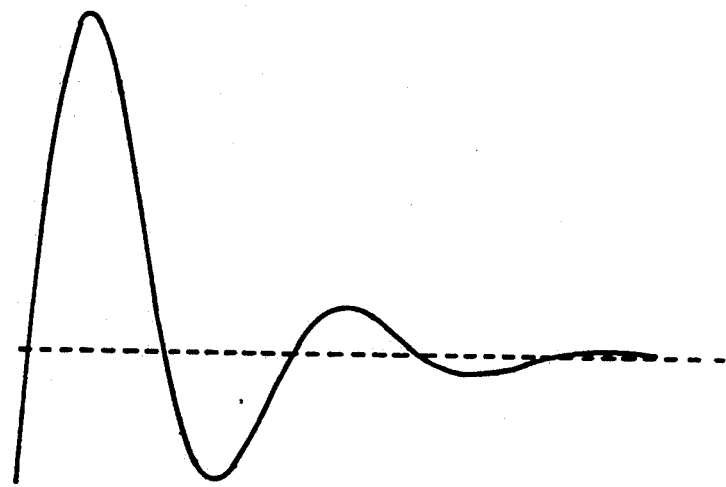
FIG. 5B is a graph of a second order term present in peripheral flow waveform.
Figure 5C:
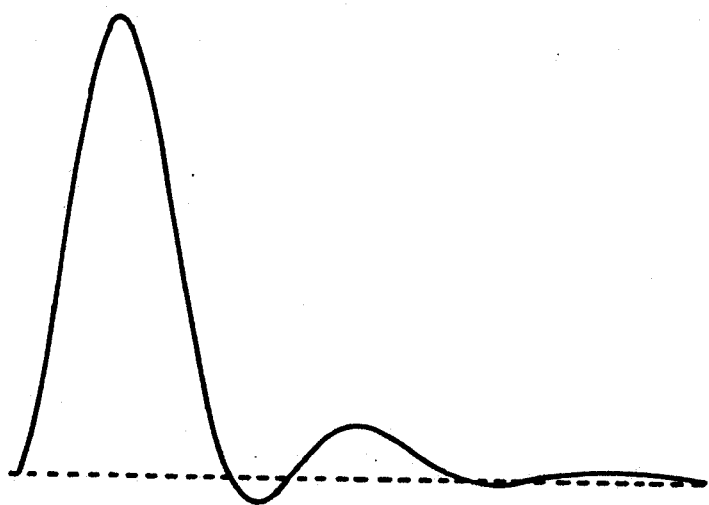
FIG. 5C is a graph of a sum of the terms of FIGS. 5A and 5B.

FIGS. 5A and 5B shows the composition of the flow velocity waveform described by Equation 15. The exponential, first order term, FIG. 5A is attributable to the aortic flow component. The oscillatory, second order term FIG. 5B is attributable to the arterial response. The combined terms $U_2(t)$, is representative of peripheral flow velocity waveforms shown in FIG. 5C.

Automated parameter-estimation algorithms have been developed to minimize the mean square error and obtain optimum fit parameters for Equation 15 in the time domain. Several additional parameters become appropriate to match time and amplitude offsets present in patient data. The parameters extracted from this time-domain parameter estimation routine for each of the proximal and distal sensor channels are:

$A_1$—scaler multiplier from aortic component
$A_2$—scaler multiplier from arterial component
$f_n$—resonant frequency (Hz) of arterial segment between aorta and peripheral site
$\zeta$—damping coefficient of arterial segment τ—decay time constant associated with aortic component offset—DC offset in patient data $t_o$—time offset between beginning of data segment and beginning systole.

Figure 6A:
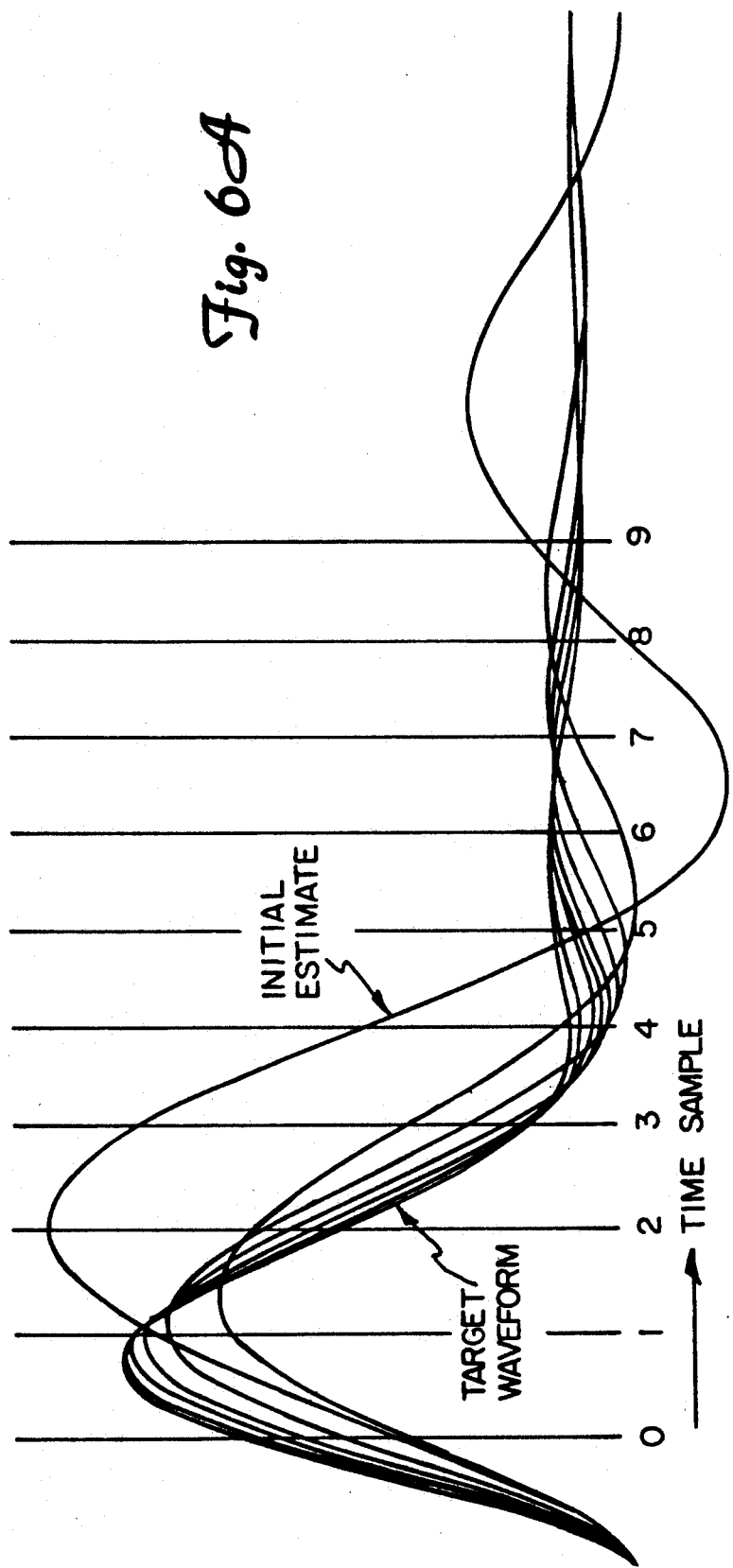
FIGS. 6A and 6B show iteratively convergence of a time domain parameter estimation algorithm.
Figure 6B:
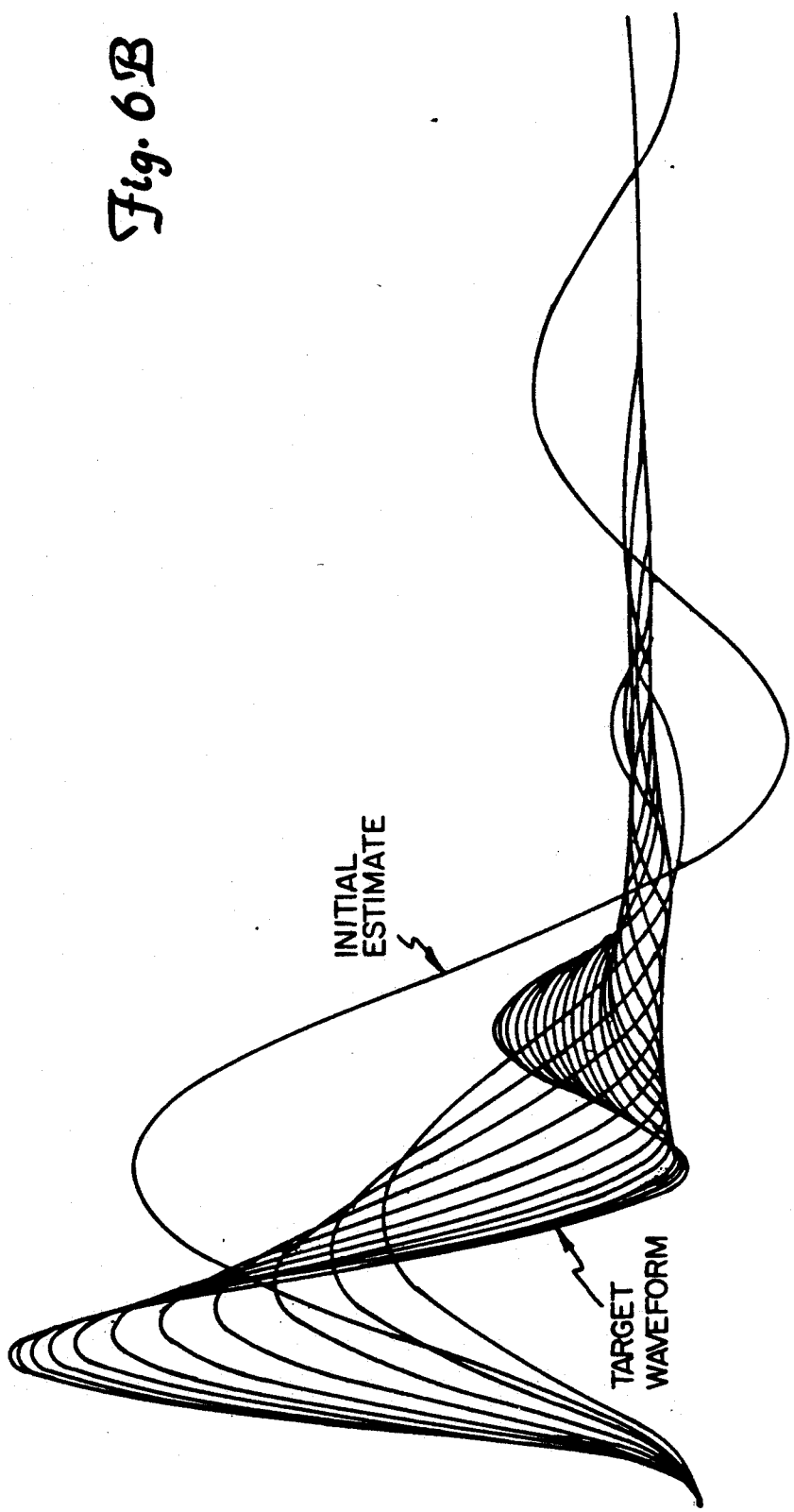

FIGS. 6A–6B show examples of the iterative convergence of the algorithm from an initial estimate of the waveform to a mathematical target waveform. FIGS. 7 and 8 show actual patient data and the optimized mathematical waveforms obtained via the parameter-estimation algorithm.

The previously discussed flow model for the arterial system (FIG. 2) can be expanded to enable calculation of arterial pressure. FIG. 8 shows the addition of the classic Windkessel, parallel resistance and compliance, to represent peripheral impedance.

Arterial pressure P(s) may be calculated as:

$$P(s) = U_2(s) Z_p(s) \quad \text{Equation 17}$$

where:

$$Z_p(s) = \left[\frac{1}{C_p}\right]\left[\frac{1}{s + \frac{1}{R_p C_p}}\right] \quad \text{Equation 18}$$

For a finite calibration time (which may be seconds or hours) the average peripheral compliance may be considered constant. Therefore, letting $k = 1/C_p$, $$Z_p(s) = \frac{k}{s + \frac{1}{P_p C_p}} \quad \text{Equation 19}$$

Equations 17 through 19 may be viewed as a first order filter with time constant, $\tau = R_p C_p$.

The impulse response of a first order filter matched to the peripheral time constant may be expressed as:

$$h(t) = e^{-at} \quad \text{Equation 20}$$

with:

$$a = \frac{1}{\tau_p} = \frac{1}{R_p C_p} \quad \text{Equation 21}$$

Pressure may now be expressed in the time domain as a convolution of $u_2(t)$ with the impulse response:

$$p(t) = u_2(t) * kh(t) \quad \text{Equation 22}$$
$$= ku_2(t) * h(t)$$

Substituting Equations 20 and 21 into 22:

$$p(t) = k \, u_2(t) * e^{-t/\tau_p} \quad \text{Equation 23}$$

with $\tau_p$ obtained from curve-fitting of the distal flow velocity waveform.

Equation 23 may be implemented via finite impulse response (FIR) digital filter techniques by convolving the flow velocity waveform, $U_2(t)$, (or an average of several beats of $U_2(t)$) with the truncated impulse response.

$$h(t) = e^{-t/\tau_p} \quad \text{Equation 24}$$

The peripheral compliance, $C_p = 1/k$, in Equations 18 and 19 becomes part of the calibration coefficient periodically calibrated as described below.

These equations may be used to compute the pressure waveform via curve-fitting parameters obtained from proximal and distal flow velocity waveforms.

$$P(s) = U_2(s) Z_p(s) \quad \text{Equation 25}$$

After substituting Equations 13 and 19 into Equation 17, the time domain representation of the pressure waveform becomes:

$$P_2(t) = \left[\frac{1}{C_p}\right]\left[\frac{K_1}{(a_2 - a_1)}\right][e^{-a_1 t} - e^{-a_2 t}] +$$

$$\left[\frac{1}{C_p}\right][K_2 G_1 + K_2 G_4(\zeta\omega_n - a_1)][e^{-a_2 t}] +$$

$$\left[\frac{1}{C_p}\right][K_2 G_2 + K_2 A_3 G_5(\zeta\omega_n - a_1)] \cdot$$

$$\left[e^{\zeta\omega_n t}\cos\omega_d t + \left(\frac{-\zeta\omega_n}{\omega_d}\right)e^{-\zeta\omega_n t}\sin\omega_d t\right] +$$

$$\left[\frac{1}{C_p}\right][K_2 G_3 - K_2 G_6(\zeta\omega_n + a_1)]\left[\left(\frac{1}{\omega_d}\right)e^{-\zeta\omega_n t}\sin\omega_d t\right]$$

with coefficients:

$$K_1 = \frac{A_1 A_2 \omega_n^2}{a_1^2 - 2\zeta\omega_n a_1 + \omega_n^2} \quad \text{Equation 27}$$

$$a_1 = \frac{1}{\tau_1} = \text{proximal time constant} \quad \text{Equation 28}$$

$$G_1 = \frac{\zeta\omega_n - a_2}{\omega_n^2 - a_2 2\zeta\omega_n - a_2} \quad \text{Equation 29}$$

$$G_2 = -G_1 \quad \text{Equation 30}$$

$$G_3 = 1 - G_1 2\zeta\omega_n \quad \text{Equation 31}$$

$$G_4 = \frac{1}{(\omega_n^2 - 2\zeta\omega_n)} \quad \text{Equation 32}$$

$$G_5 = -G_4 \quad \text{Equation 33}$$

$$G_6 = -G_4(2\zeta\omega_n) \quad \text{Equation 34}$$

Figure 9:
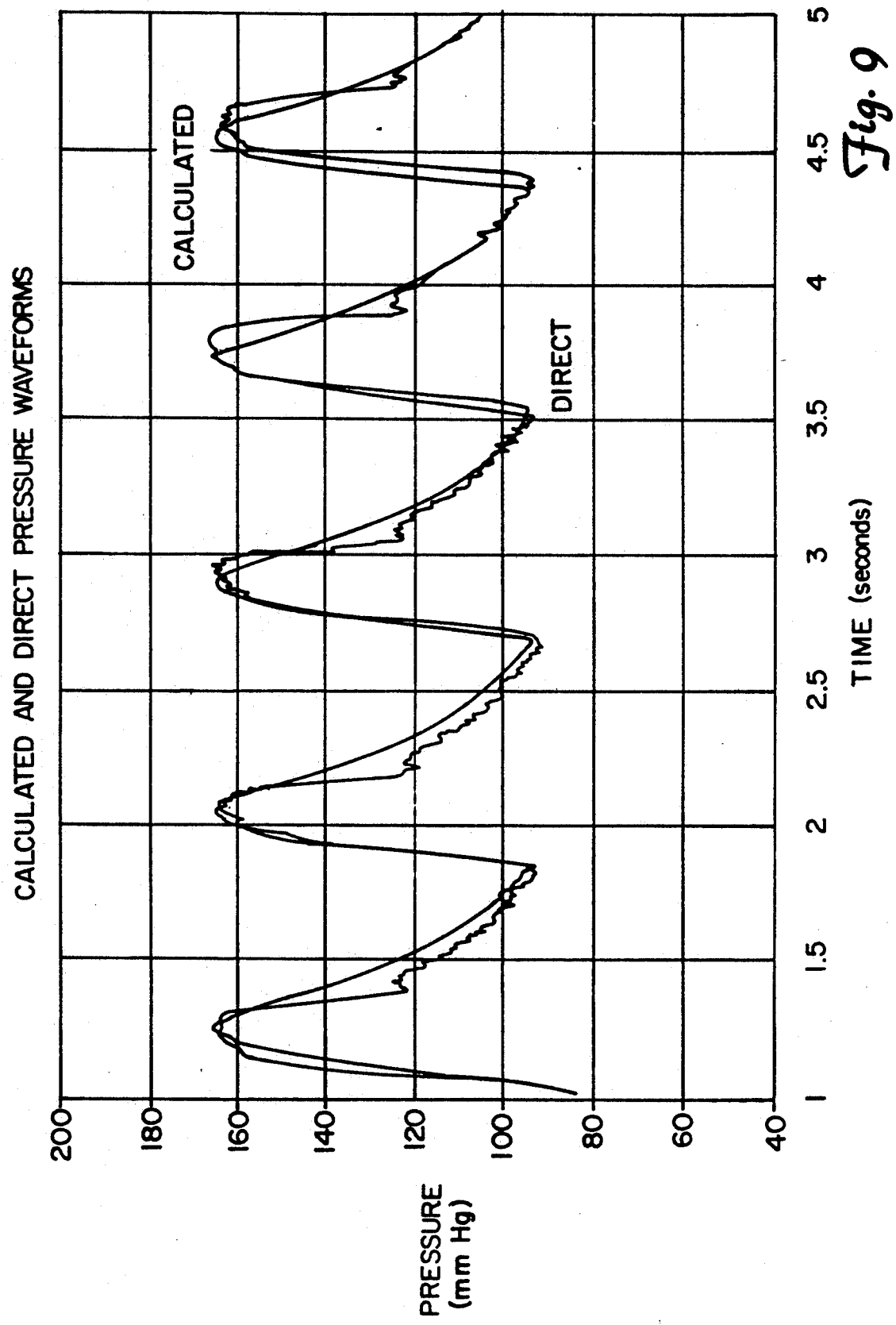
FIG. 9 is a comparison of calculated blood pressure and directly measured blood pressure.
Figure 10:
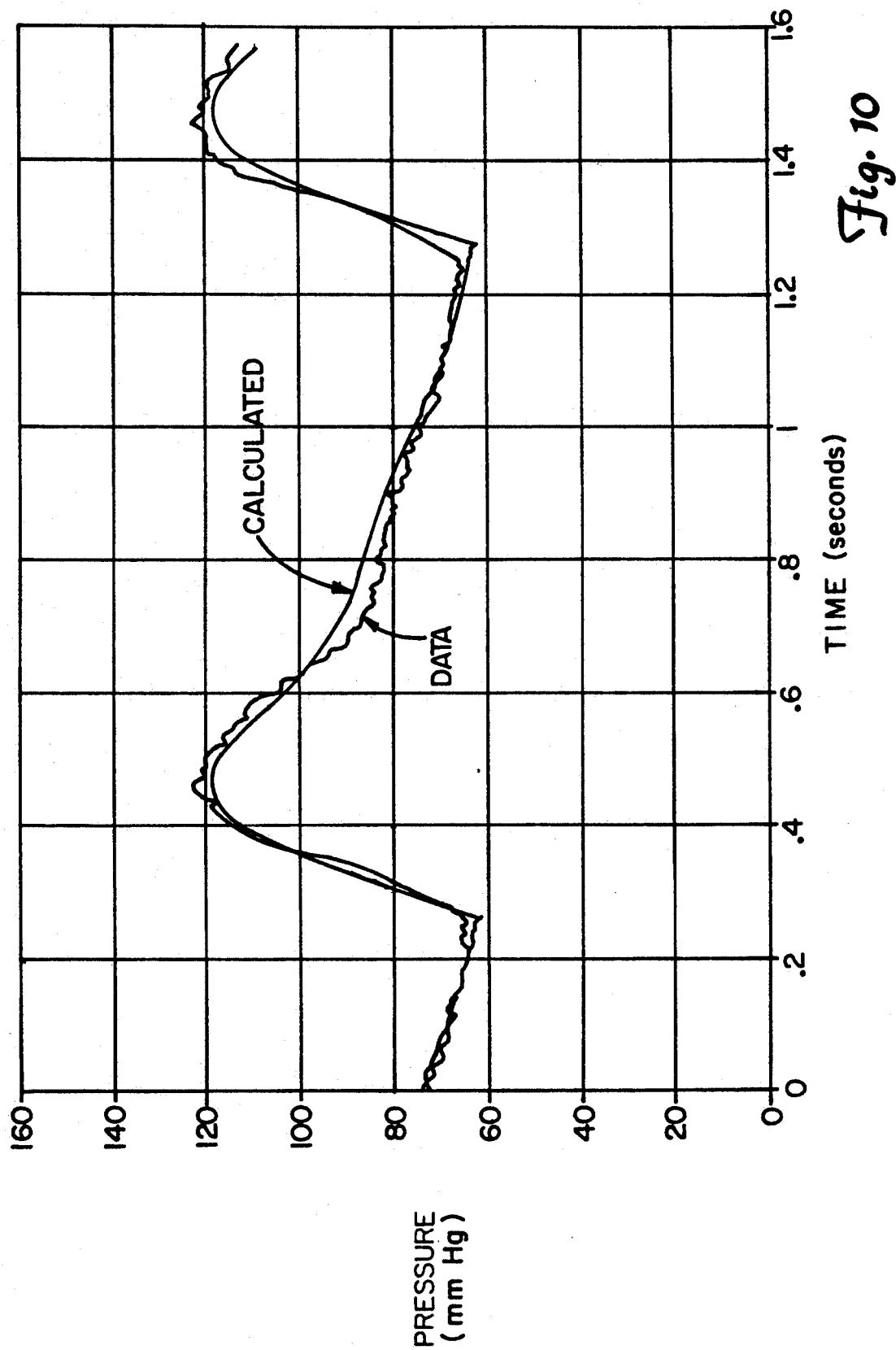
FIG. 10 is a comparison of calculated blood pressure and directly measured blood pressure.

FIGS. 9 and 10 show pressure waveforms calculated from arterial curve-fitted parameters and Equations 26 through 34.

IV. Description of System Operation (1) Monitor 10 (FIG. 1)

The sensor function is performed by continuous-wave, doppler-ultrasound proximal and distal sensors 14 and 16, which are placed over the brachial and ulnar (or radial) arteries, respectively, as shown in FIG. 1. These piezoelectric sensors obtain flow velocity signals which contain the physiological information necessary to characterize properties of the arterial system.

The high frequency blocks 20A and 20B include ultrasonic drivers, high-gain receivers, analog bandpass filters, and high frequency quadrature circuitry necessary to obtain bi-directional doppler flow-velocity waveforms.

The doppler processing blocks 22A and 22B contain filters to remove wall and skin motion artifacts, an automatic gain control to permit interchangeability of sensors, a frequency detector, a bi-directional detector to permit determination of flow direction, and a frequency-to-voltage converter to enable the magnitude of the flow velocity to be established.

The flow velocity processing blocks 24A and 24B contain linear-phase, low-pass filters to further increase the signal-to-noise ratio while maintaining phase integrity of the flow velocity signals. This block also includes a calibration amplifier which is set to output the flow velocity signal calibrated at 1 volt per 1000 Hz according to the ultrasonic carrier frequency and angle of doppler intersect.

The digital preprocessing blocks 26A and 26B include an analog-to-digital converter, digital low-pass filter, beat-detection function, peak alignment segment, and beat averaging sections in order to provide the next block with an averaged, high quality signal representative of the heartbeats within the time window of interest.

The parameter estimation blocks 28A and 28B employ a least-squares iterative algorithm to compare the acquired flow velocity waveform at each sensor site to that predicted from the mathematical model of the arterial system. The mathematical parameters from the model are evaluated in this manner to reflect the arterial characteristics.

The waveform generation block 30 employs a combination of arterial parameters and temporal arterial resonant frequencies to generate an arterial pressure waveform in units of arterial resonant frequency in Hertz.

The calibration function block 32 utilizes the most accurate features of noninvasive cuff techniques to convert the calculated arterial pressure waveform in units of Hertz to more widely accepted units of mmHg.

The display function 38 may be a digital display of systolic, mean, and diastolic pressures, a digital display of calibrated pressure waveforms on a cathode ray tube or liquid-crystal display, or an electronic emulation of a pressure transducer permitting connection of this product to standard central monitoring stations in an intensive care unit (ICU) or other hospital environment.

(2) Proximal and Distal Sensors 14 and 16

The function of each sensor 14 and 16 placed over a given arterial site is to obtain signals which contain sufficient information about the underlying artery. The signal-to-noise ratio of these sensor signals must be high enough to enable the extraction of arterial parameters with acceptable accuracy.

While a number of sensor technologies may potentially be applied to this duty, bi-directional doppler ultrasonic sensors were chosen to monitor blood flow velocity within the artery because of the following advantages:

a) The flow velocity waveform was observed to exhibit the same resonant frequency characteristics as the underlying artery;

b) The doppler signal-to-noise ratio is approximately 30 dB, which permits accurate extractions of the arterial characteristics via digital signal processing means;

c) Flow velocity doppler signals may be electronically filtered to remove wall motion and skin-sensor motion thus permitting ambulatory monitoring of patients;

d) Locating the doppler sensor over the artery is simplified because the sensor position may be optimized by selecting the location yielding the maximum doppler sound amplitude;

e) Ultrasonic sensors may be employed without any occlusion of the artery as would be necessary in a fully or partially inflated cuff or any type of external pressure transducer used in tonometers; and f) The cost and size of such sensors is attractive for a device such as this.

Specifically, each doppler sensor consists of a transmitting and a receiving piezoelectric transducer used to generate and receive continuous-wave signals from the moving blood within the artery. The proximal doppler sensor was chosen to operate at a frequency of 5 MHz and the distal sensor was chosen to operate at a frequency of 6 MHz. The different operating frequencies permit sensor operation in close proximity to each other without cross-coupling of signals. The ultrasonic output of the sensors in maintained below the regulatory limit of 100 mW per square centimeter of skin surface area.

The transmitter element in each sensor is driven by a high frequency signal and generates a continuous-wave ultrasonic wave which insonifies the artery of interest. The receiving element of each sensor receives the ultrasonic energy which has been reflected off of the moving blood cells within the artery. This low-level received signal is shifted by the doppler frequency. As a practical matter, the unshifted carrier frequency is also present at the receiving crystal due to capacitive feedthrough from the transmitting circuitry and crystal. The received signal may be as much as 40 to 60 dB below the unshifted carrier. These high frequency signals are then processed to obtain the desired doppler signals.

Each sensor is held in position during the extended monitoring period by elastic wrap, elastic straps, or adhesive tape.

Figure 11:
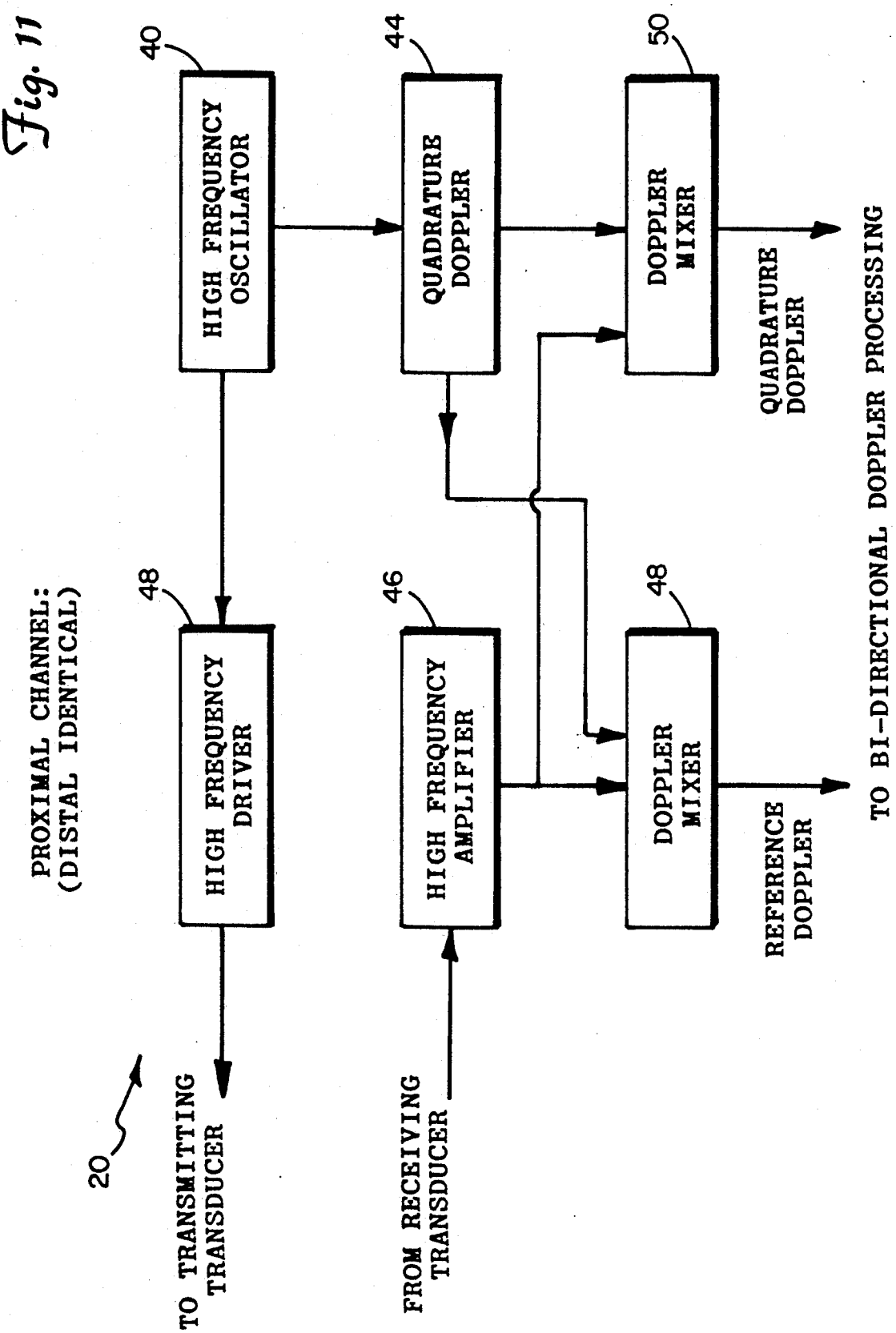
FIG. 11 is a block diagram of a high frequency processing stage.

(3) High Frequency Analog Processing Circuits 20A, 20B (FIG. 11)

FIG. 11 is a block diagram of analog processing circuit 20A. Circuit 20B has an identical block diagram. In this and following sections, circuit blocks 20A-28A will be described, with the understanding that the diagrams of FIGS. 11-15 are equally applicable to circuit blocks 20B-28B.

The continuous-wave, ultrasonic signal is initially generated by stable crystal oscillator 40 of FIG. 11, in the 4 to 8 MHz range. The oscillator signal is buffered by wideband, low impedance output driver 42 in FIG. before it energizes the piezoelectric transmitting transducer of sensor 14.

The ultrasonic energy reflected from the moving blood cells after being received by the piezoelectric receiving transducer of sensor 14 is converted to electrical energy with doppler sidebands above or below the transmitted carrier signal (depending upon flow direction). This weak, high-frequency signal is amplified by high-gain, wideband amplifier 46. Quadrature generator 44 generates two high-frequency signals which are 90° out of phase with each other for the purpose of generating the bi-directional flow velocity desired from this circuitry. These quadrature signals are fed into the mixers 48 and 50 of FIG. 11. This mixing process, which includes suppression of the high-frequency component generated, results in reference and quadrature doppler signals which are 90° out of phase with each other. These two doppler signals are then input to bi-directional doppler processing circuit 22A of FIGS. 1B and 12 for additional processing.

Figure 12:
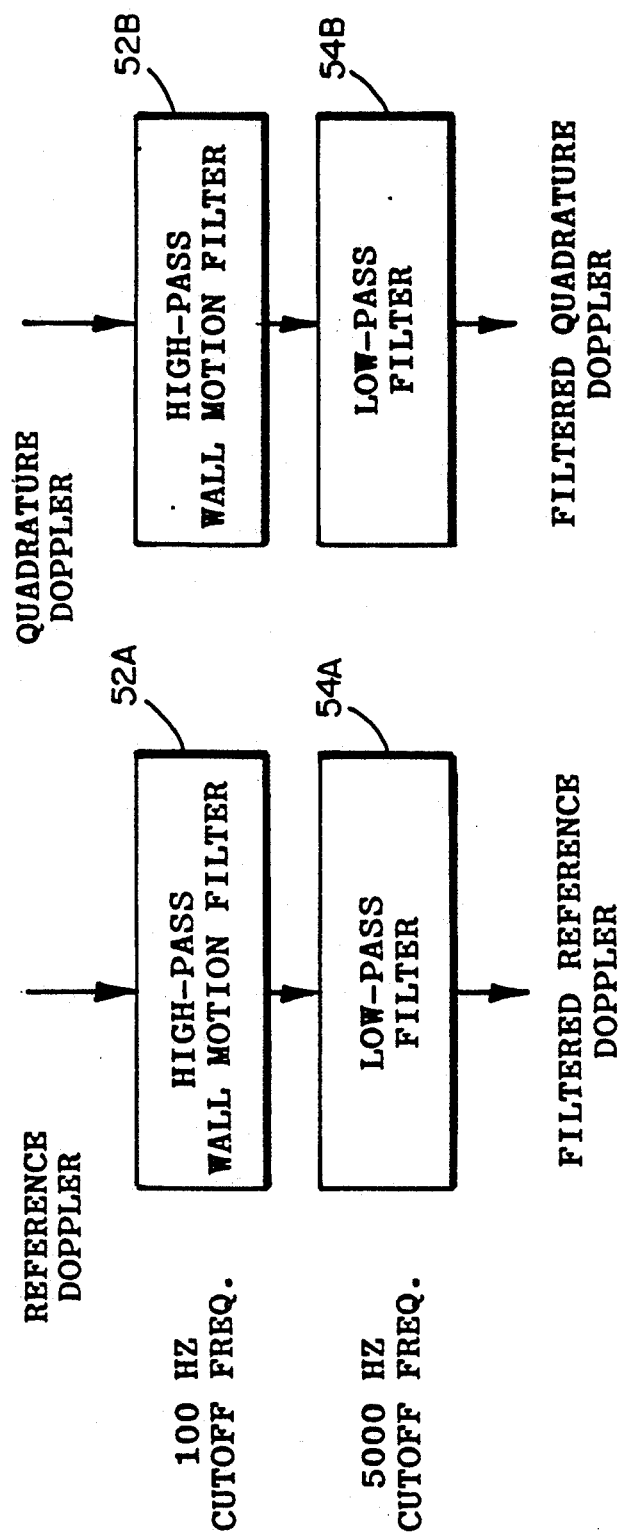
FIG. 12 is a block diagram of a bi-directional doppler processing stage.

(4) Analog Doppler Processing 22A and 22B (FIG. 12)

FIG. 12 is a block diagram of analog processing block 22A. Block 22A filters the doppler signals from block 20A to preserve the desired signals and minimize frequency components generated by motion or noise sources. Upon entering block 22A, the signals are filtered by high-pass networks 52A and 52B, which have a cutoff frequency of 100 Hz. This high-pass filtering removes most of the low frequency components attributable to motion of the arterial wall or motion of the skin/sensor interface. Next, these signals are filtered by low-pass filters 54A and 54B to remove high-frequency noise and yet preserve the desired doppler bandwidth of 100 Hz to 5000 Hz. The filtered reference and quadrature doppler signals are then passed to velocity processing block 24A of FIG. 1B.

Figure 13:
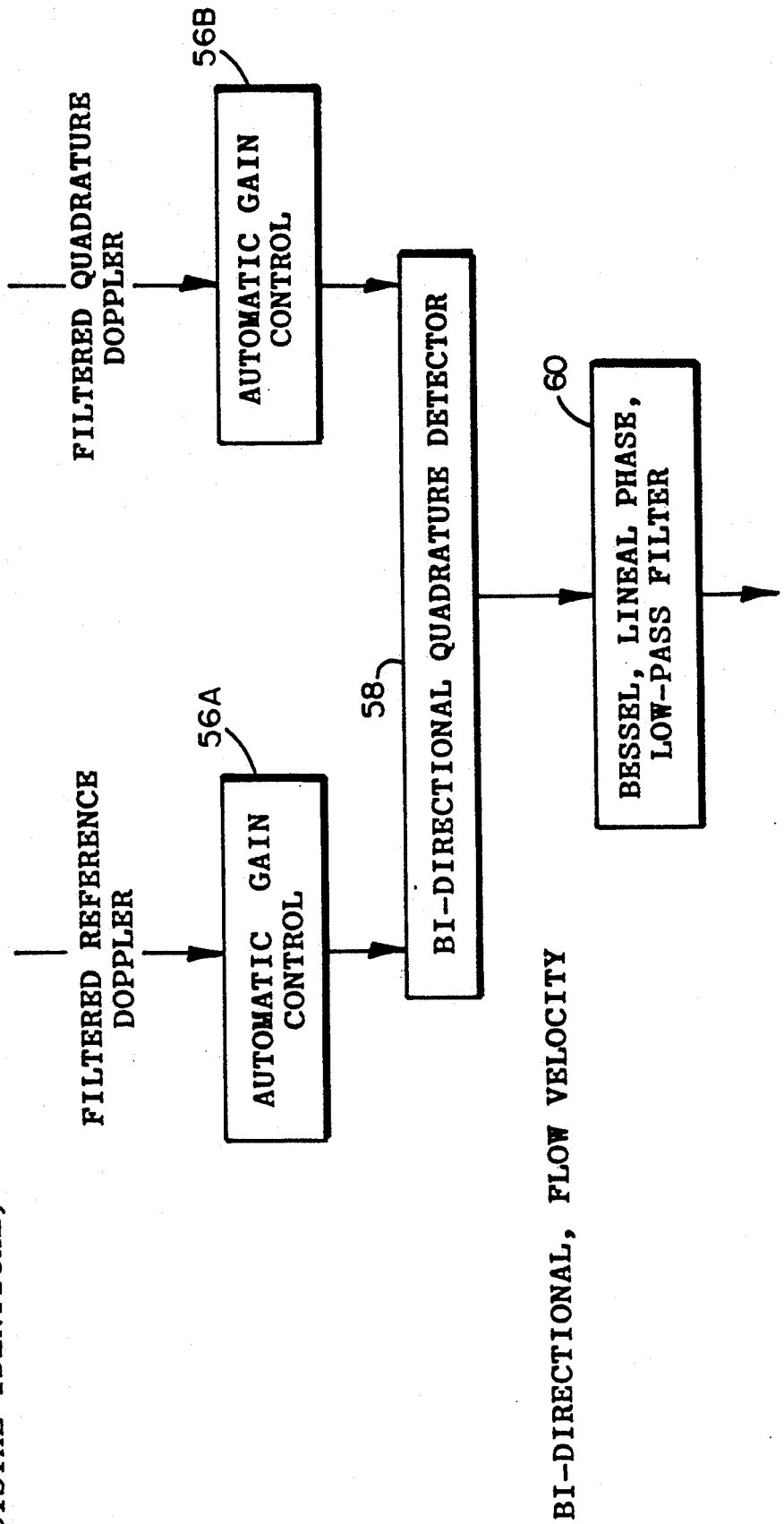
FIG. 13 is a block diagram of an analog flow velocity processing stage.

(5) Analog Flow Velocity Processing 24A, 24B (FIG. 13)

Upon entering analog flow velocity processing block 24A of FIGS. 1B and 13, the filtered quadrature and reference doppler signals are operated upon by the automatic gain control (AGC) blocks 56A and 56B of FIG. 13. This AGC function equalizes signals of differing amplitudes. The net result of this function is a system which is more robust and is less sensitive to factors such as sensor efficiency or patient obesity. Clinically, sensor interchangeability and patient interchangeability are significantly improved as a result of the AGC blocks 56A and 56B.

After amplitude normalization, the filtered reference and quadrature doppler signals are processed by a quadrature bi-direction doppler detector 58. The output of detector 58 is a bi-directional flow velocity signal.

The flow velocity signal is filtered with a linear-phase, low-pass Bessel filter 60 having a cutoff frequency of 12 Hz. It is important that this filter be linear phase since the phase integrity of the flow velocity signals is very important during the parameter estimation processing. The bandwidth is selected to pass substantially all of the major frequency components while rejecting any remaining doppler frequency components and further improving the signal-to-noise ratio.

The output from filter 60 is a filtered, bi-directional, flow velocity signal ready for digitization and further processing in digital preprocessing block 26A.

Figure 14:
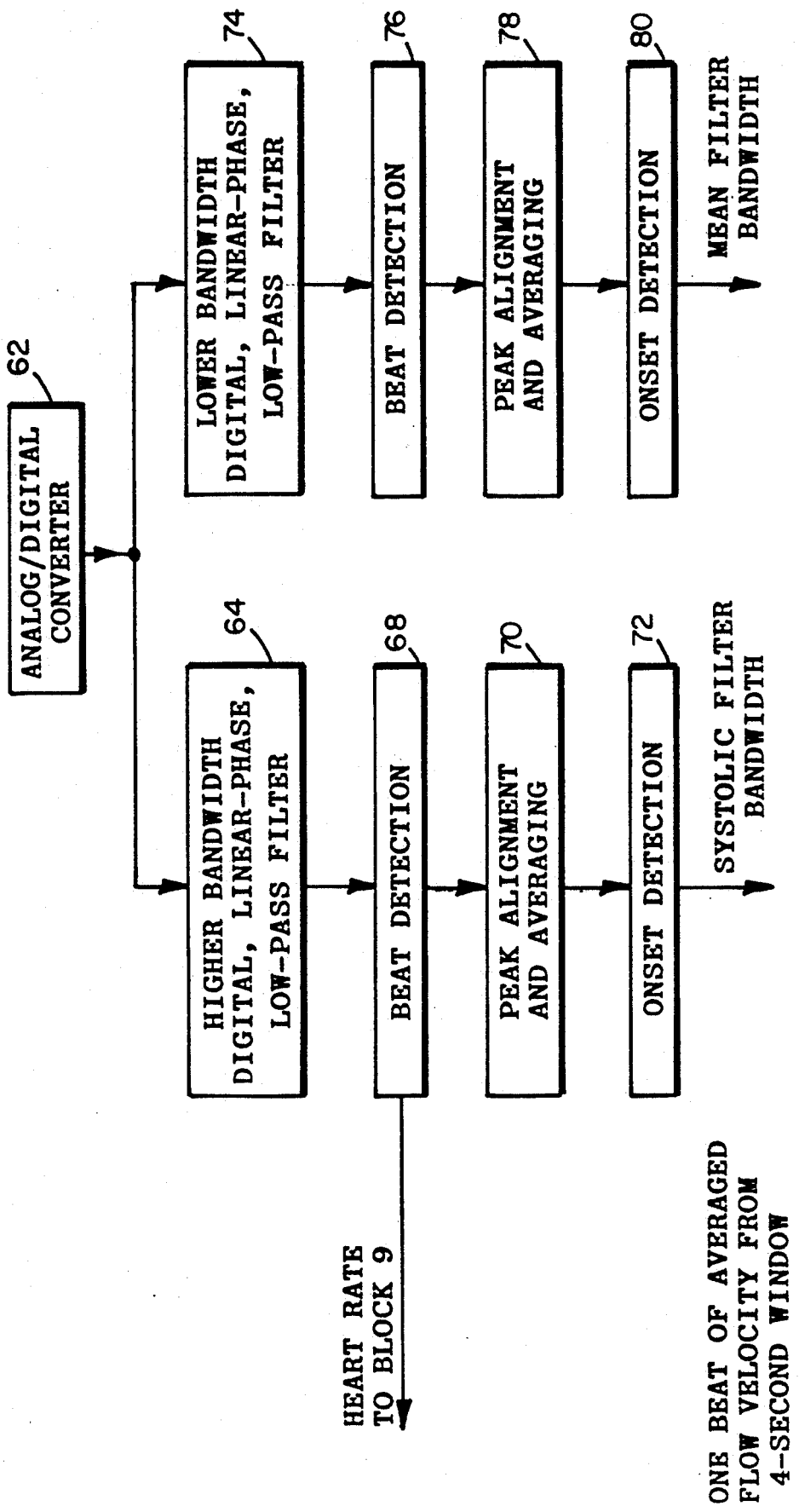
FIG. 14 is a block diagram of a digital preprocessing stage.

(6) Digital Preprocessing Blocks 26A, 26B (FIG. 14)

The filtered, bi-directional, flow velocity signal from block 24A is applied to digital preprocessing block 26A (FIG. 14) and digitized via an analog-to-digital (A/D) converter 62. The sampling rate of A/D converter 62 is 128 Hz with A/D resolution of 12 bits. The digitized flow velocity signal is then filtered by two different linear-phase, low-pass filters 64 and 74. Low-pass filter 64 has a cutoff frequency of approximately 5 Hz and provides the signal used in the estimation of mean pressure parameters. Low-pass filter 74 has a cutoff frequency of approximately 10 Hz and provides the signal used in the estimation of systolic pressure parameters.

The mean pressure signal filtered by low-pass filter block 64 enters a beat-detection block 68 in which each cardiac cycle is identified. The beats identified as part of this function, as well as the initial signals, are passed on to the onset detection block 72. The heart rate determined within beat detection block 68 is also passed to the display section 38 for display of heart rate.

Each detected beat from beat detection block 68 is passed to averaging block 70 of FIG. 14. The peak of the flow velocity waveform in each cardiac cycle is identified and all the complete beats within a four-second window are aligned according to these peaks and averaged. The single-beat flow velocity waveform resulting from this alignment and averaging process is passed on to onset detection block 72 in order to precisely determine the beginning of the cardiac cycle.

The onset detection block 72 provides a refined determination of the precise location of the beginning or "onset," of the average beat output from averaging block 70. Initially, the slope of the flow velocity waveform is calculated. Moving in the direction of increasing time, the point at which the slope exceeds 14% of its peak value is used as an initial estimate of the beginning of systole. Within the vicinity of the threshold first derivative, the second derivative is calculated. The peak second derivative, or time of greatest increase in acceleration of the blood cells, is taken as the best estimate of systolic onset. Further refinement in the determination of the onset includes interpolation between sampling points.

Processing blocks 64, 68, 70 and 72 of the mean pressure channel are duplicated with only the filter bandwidth increased in blocks 74, 76, 78 and 80 for the systolic pressure channel.

At the conclusion of the preprocessing steps, the averaged waveform, together with its precise onset location is passed to the parameter estimation circuit 28A in FIG. 1B.

Figure 15:
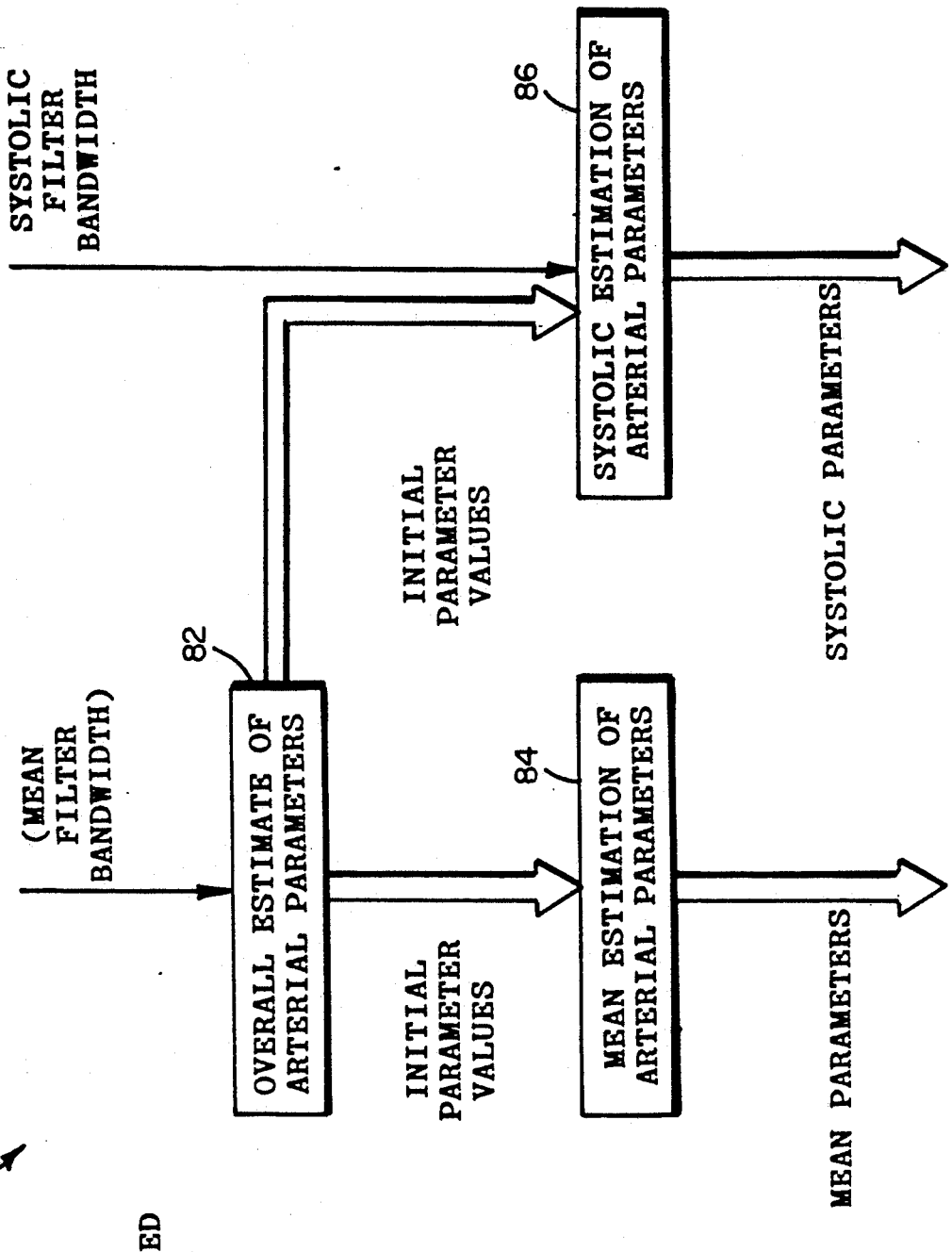
FIG. 15 is a block diagram of a parameter estimation stage.

(7) Parameter Estimation Blocks 28A, 28B (FIG. 15)

The aligned and averaged cardiac cycles from FIG. 14 are input into the processing blocks of parameter estimation block 28A as shown in FIG. 15. The following parameters are estimated via a minimum least-squares error process in each of the functional blocks of FIG. 15.

$A_1, A_2$—Amplitude constants;
tau—time constant;
$f_n$—resonant frequency of the artery; 1
zeta—damping coefficient;
$t_o$—time offset from the determined onset; and
offset—level shift added to the waveform to obtain the mathematical onset level requirement.

The mathematically-generated flow velocity waveform and its explicit partial derivatives, per the flow model of the artery, are compared to the data waveforms in these iterations to determine the parameters of interest.

The low-bandwidth cardiac cycle from the mean pressure filter of circuit 26A is first used to estimate the best parameter values over the entire flow velocity waveform in the time domain as indicated in block 82 of FIG. 15. The parameters generated from estimate block 82 are in turn used as initial conditions for application of the MSE estimate of parameter values within mean estimate block 84 and systolic estimate block 86.

The mean estimate block 84 parameter estimate is conducted using the magnitude of the frequency domain representation of the signal. Alternately, the mean pressure parameters may be obtained by fitting the time segment of the temporal flow velocity waveform occurring simultaneously with the mean pressure.

The parameters determined during the best overall parameter estimate (block 82) are also used in conjunction with the wide-band cardiac cycle from the systolic pressure filter of circuit 26A. The systolic parameters are determined by applying the MSE technique to the wide-band, time-domain flow velocity waveform during the systolic period of the cardiac cycle. In this manner, arterial parameters are determined which apply to the peak or systolic pressure within the arterial system.

Figure 16:
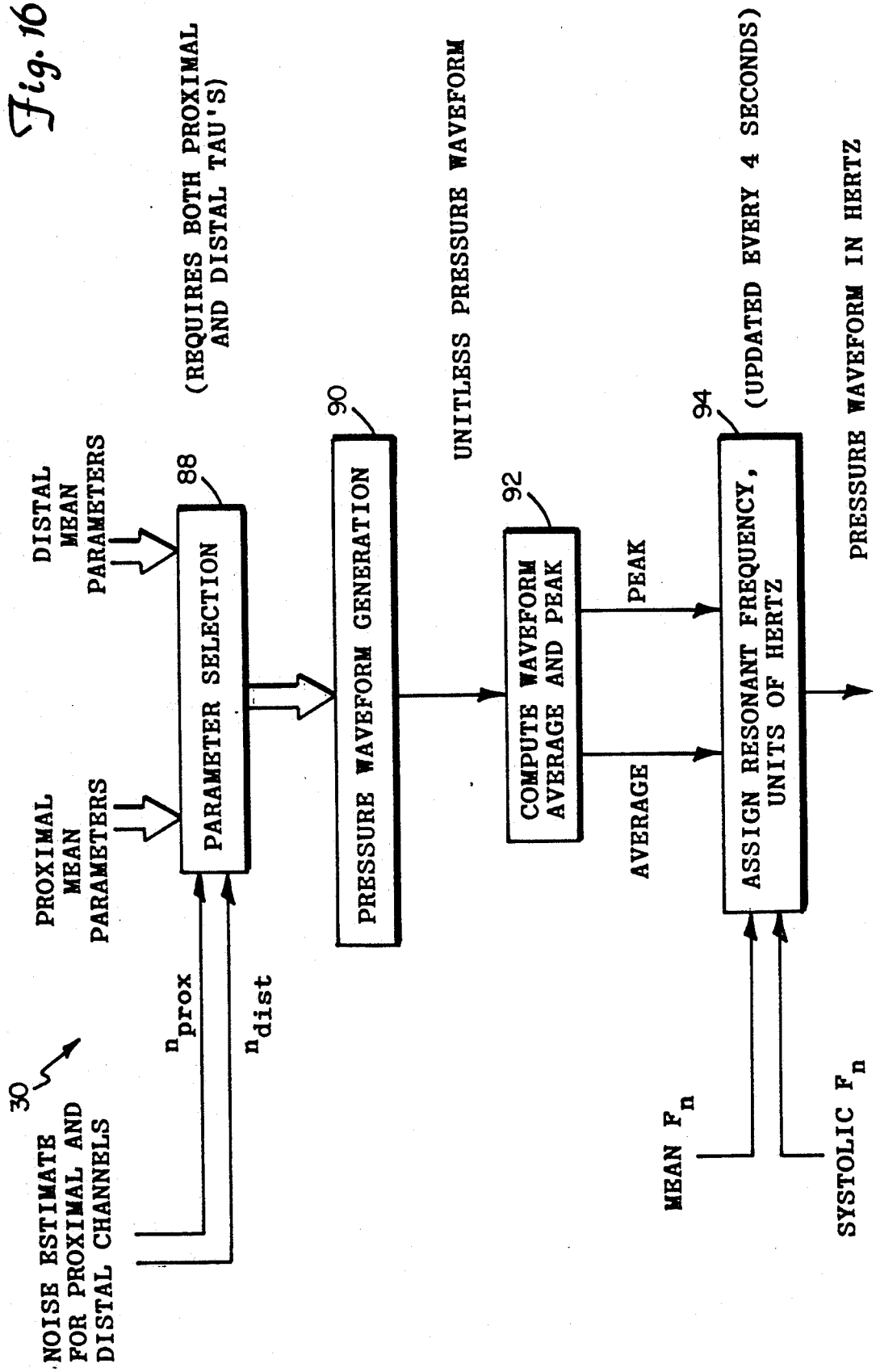
FIG. 16 is a block diagram of a pressure waveform generation stage.

(8) Pressure Waveform Generation (FIG. 16)

The pressure waveshape may be generated from the above equations via the matched filter technique or the mathematical derivation. The mathematical derivation was found to be less sensitive to the beat-to-beat waveform variability since the parameters are averaged over a 4-second window (typically 4-6 beats).

Proximal or distal mean parameters, $A_1$, $A_2$, tau, zeta, $F_n$, $t_o$, and offset are candidates for generating the waveform as indicated in parameter selection block 88 of FIG. 16. The most appropriate selection criteria between the two sensor sources is signal-to-noise ratio (SNR) of the initial sensor signals.

The mean parameters from the selected sensor channel in addition to the decay time constant from the alternate channel are then used to compute the pressure waveform equations by waveform generation block 90. The resulting waveform strongly resembles that of arterial pressure.

In Average and peak block 92 of FIG. 16, the temporal waveform average and the peaks are calculated and identified. These values are paired with the mean and systolic resonant frequencies obtained via parameter estimates from each data window (block 94). For a four-second data window, this parameter assignment is updated every four seconds. The output of the processing from waveform generation block 30 in FIGS. 1 and 16 is therefore a waveform expressed in units of resonant frequency which has a shape identical to that of the arterial pressure waveform. It provides the conversion from units of resonant frequency to units of pressure, namely mmHg.

Figure 17:
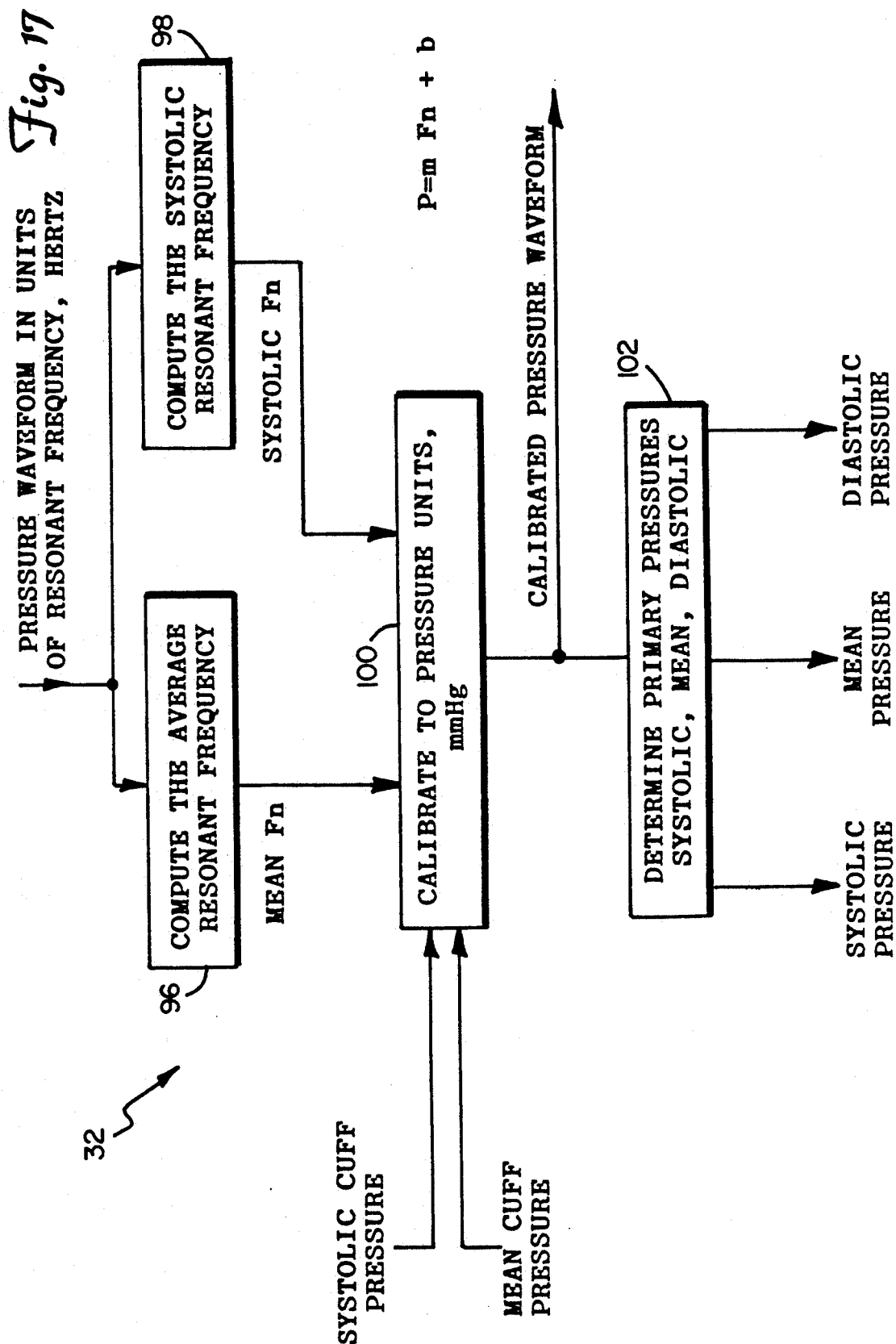
FIG. 17 is a block diagram of a calibration stage.

(9) Calibration Block (FIG. 17)

FIG. 17 is a block diagram of calibration block 32. The average resonant frequency and the systolic resonant frequency of the waveform are computed as indicated in FIG. 17 (blocks 96 and 98). The corresponding systolic and mean pressures, in mmHg, are available from a noninvasive, occlusive cuff calibration, the strengths of which are described below. The solution of two simultaneous linear equations yields the calibration equation which converts the resonant frequency units of Hertz (Hz), into the commonly accepted pressure units, millimeters of mercury (mmHg). This calibration equation may be expressed as:

$$P(t) = m \, F_n(t) + b \qquad \text{Equation 35}$$

Where, $F_n(t)$ is the time-varying resonant frequency of the artery in units of Hertz; P(t) is the time-varying arterial pressure in mmHg; m is the calibration factor in units of mmHg per Hertz; and b is the pressure offset in mmHg.

Based upon the mean $F_n$, the systolic $F_n$, the mean cuff pressure, the systolic cuff pressure, and Equation 35, calibration block 100 calibrates the pressure waveform to units of mmHg. In block 102, the systolic pressure, mean pressure and diastolic pressure (in mmHg) are derived from the calibrated pressure waveform.

While the calibration of this system depends in part on the accuracy of the cuff measurement of systolic and mean pressures, this system has significant accuracy advantages over many other automated cuff systems. This system's cuff pressure is slowly reduced from a value above systolic pressure, while the two flow velocity sensor signals are monitored. As the cuff pressure reaches systolic pressure, the sensitive flow velocity sensors 14 and 16 positively detect the first spurt of blood past the occlusive cuff 34. The cuff pressure at the time of the initial distal flow is tightly linked to systolic pressure. After review of numerous approaches to determine mean arterial pressure via the cuff 34, the common oscillometric method was selected. At the time of peak cuff oscillations, the cuff pressure is equal to the mean arterial pressure as discussed above. Reliability of the calibration is further enhanced via this approach since the "peak" cuff oscillations provide a measurement during the greatest signal-to-noise ratio available. Additional accuracy is obtained by limiting the cuff deflation rate to approximately 3 mmHg per heart beat. Since this system requires only infrequent calibrations, the reduction in speed to obtain increased calibration accuracy is a wise tradeoff. Automated cuff systems which must inflate and deflate the cuff on a very frequent basis would significantly sacrifice clinician convenience if such a slow inflation rate was regularly employed in the systems.

Figure 18:
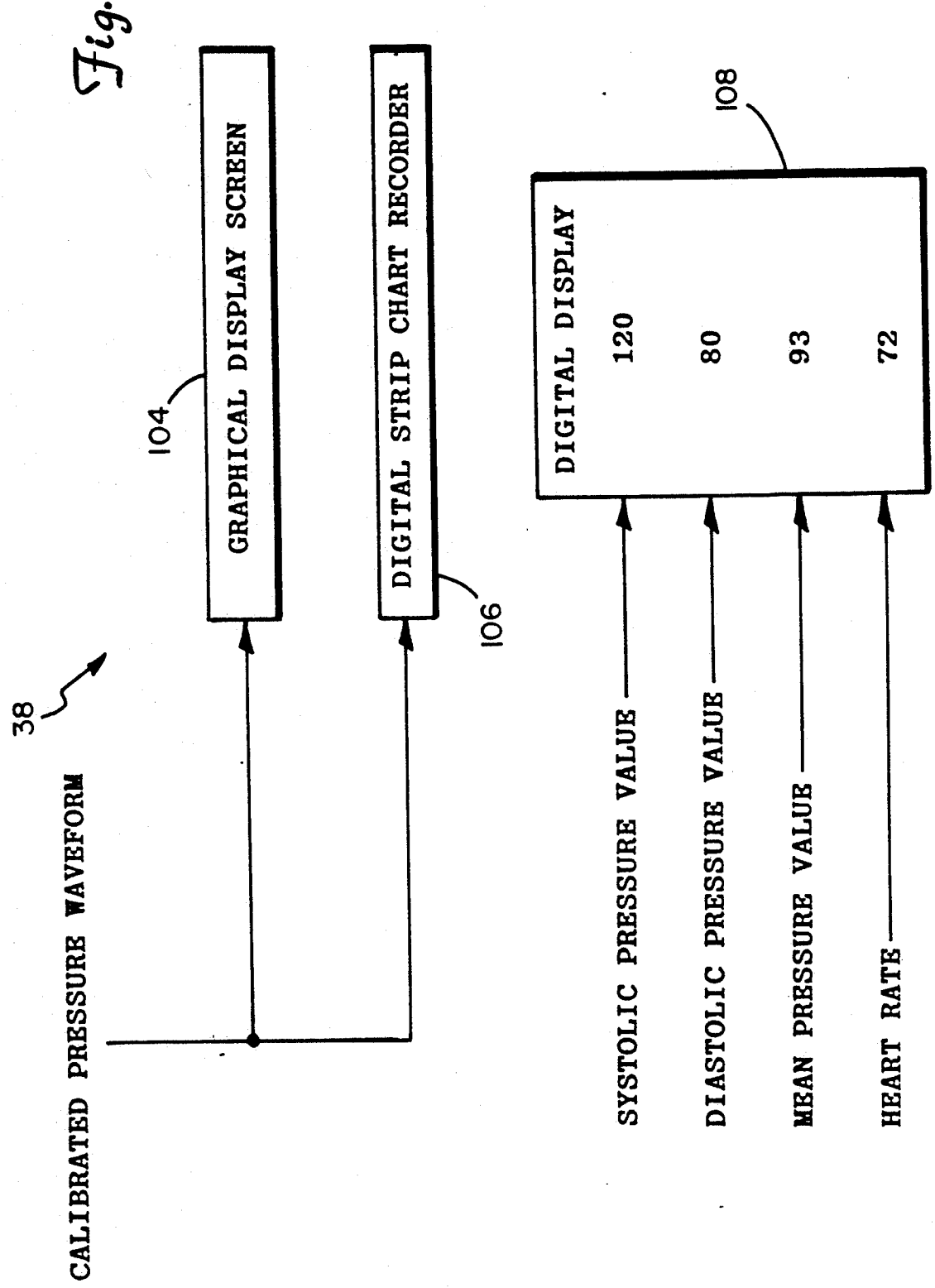
FIG. 18 is a block diagram of a display stage.

(10) Display 38 (FIG. 18)

FIG. 18 is a block diagram of display 38. The calibrated pressure waveform and significant pressure values may be displayed via several methods as indicated in FIG. 18 including graphical display screen 104, strip chart recorder 106 and digital display 108.

The discrete values of systolic, mean and diastolic pressures are available for digital display 108 on the face of an instrument via light-emitting diodes (LED), liquid crystal displays (LCD), or similar technologies. The value of the heart rate may be similarly displayed.

The calibrated pressure waveform may be displayed via analog or digital format on numerous graphical display media such as a cathode-ray tube (CRT), liquid crystal display (LCD) array, gas-plasma discharge unit, a electro-luminescence screen, or a strip chart recorder.

The calibrated pressure waveform may also be input to central monitoring stations, common in intensive care units, by using the calibrated pressure waveform to modulate an electronic circuit which simulates the direct pressure transducer typically used for monitoring arterial pressure invasively. With this approach, the clinician has the advantage of obtaining a calibrated pressure waveform on a central monitoring station without the risk and expense of the invasive surgical procedure.

V. Alternative Embodiments

The preferred embodiments described in Section IV have been selected for their stated advantages. However, alternative embodiments exist and are described herein. The present invention includes a number of alternative embodiments.

(1) Alternative Sensors for Obtaining the Pressure Waveshape

The method and apparatus for obtaining the pressure waveshape using ultrasonic doppler sensor inputs was described above. However, alternative sensors may be employed. Examples of additional sensor systems which may be used to obtain a general pressure wave shape include:

a) Impedance plethysmography techniques;
b) An infrared perfusion sensor;

c) Continuous oscillations in a partially or fully inflated cuff;
d) Pressure transducers or strain-gauge devices applied against the arterial wall;
e) Ultrasonic imaging techniques which provide the time-varying arterial diameter or other arterial geometry which changes proportionately with intra-mural pressure;
f) Radio frequency sensors; or
g) Magnetic field sensors.

Figure 19:
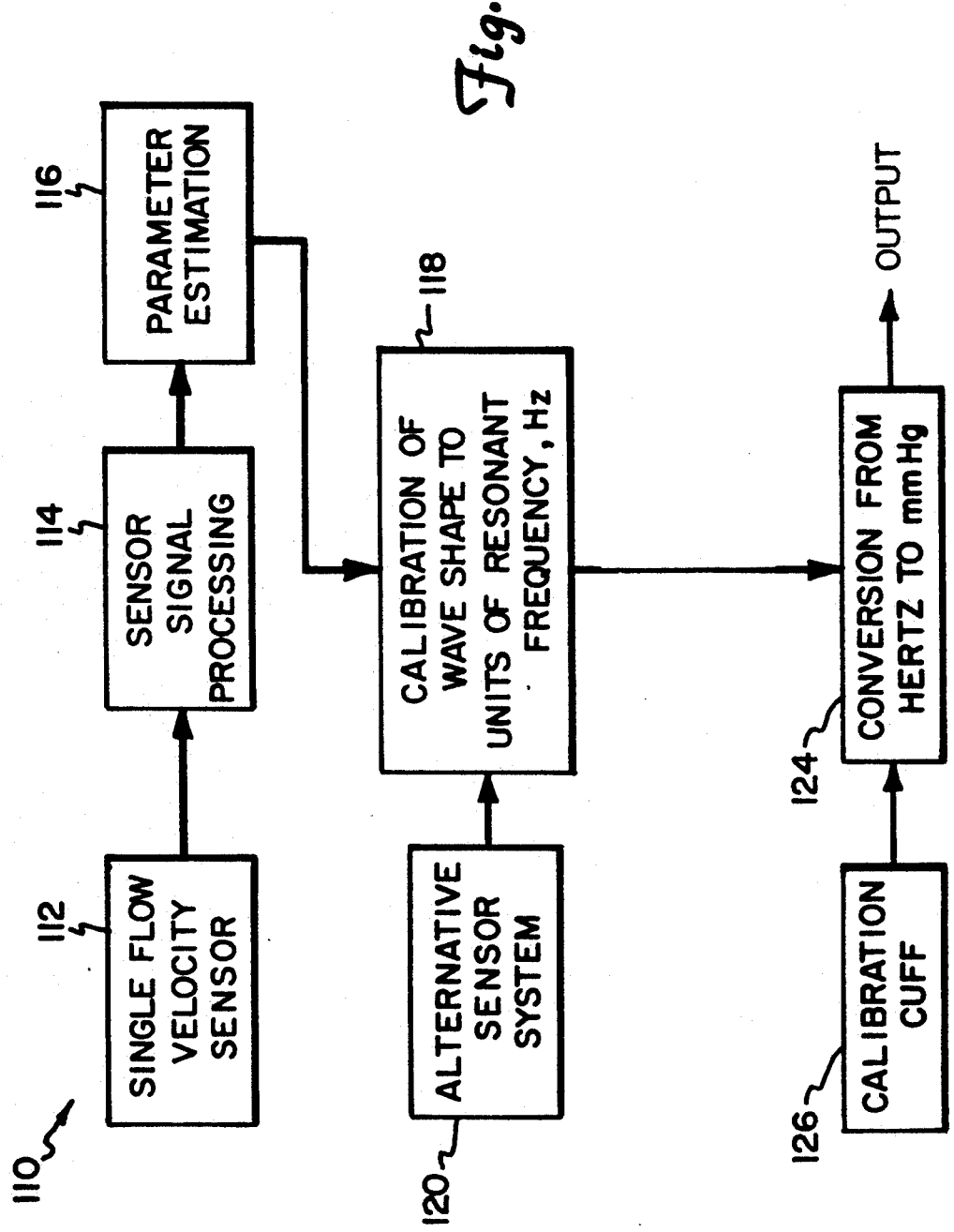
FIG. 19 shows a block diagram of waveform generation circuitry which uses alternative sensors.

FIG. 19 is a block diagram of circuitry 110 of waveform generation circuitry using alternative sensors and calibration with a single flow velocity sensor. In FIG. 19, circuitry 110 includes a flow velocity sensor 112. The output of the sensor is applied to a sensor processing circuit 114 and parameter estimation circuit 116. The output on parameter estimation circuit 116 is received by calibration circuit 118. Calibration circuit 118 also receives an input from an alternative sensor system 120. This may comprise various different types of sensors such as the examples listed above. Calibration circuitry 118 is used to calibrate the output to units of Hertz. This is converted from Hz to millimeters of mercury via circuit 124. Conversion circuit 124 receives calibration information from calibration cuff 126. Conversion circuit 124 provides an output to pressure waveform calibration circuit 128.

Regardless of the sensor selected to provide the general, uncalibrated pressure waveshape, the calibration method of FIG. 19 provides a means of converting the uncalibrated waveshape into a calibrated arterial pressure indicator. The waveshape maximum and time average are determined on a beat-by-beat basis in wave shape units. The conversion from waveshape units to resonant frequency units is accomplished via the solution of simultaneous linear equations 36 and 37:

$$f_{nsys} = m^*(\text{waveformmaximum}) + b \qquad \text{Equation 36}$$

$$f_{navg} = m^*(\text{waveformaverage}) + b \qquad \text{Equation 37}$$

Where, $f_{nsys}$, is the systolic resonant frequency of the artery as computed from a single doppler flow velocity signal. $F_{navg}$, is the time average value of the sensor waveform. The conversion coefficients, m and b, are the slope and intercept of the conversion equation 38.

$$f_n = m^*(\text{waveform value}) + b \qquad \text{Equation 38}$$

The further conversion of resonant frequency units to pressure units is accomplished as described above.

Figure 20:
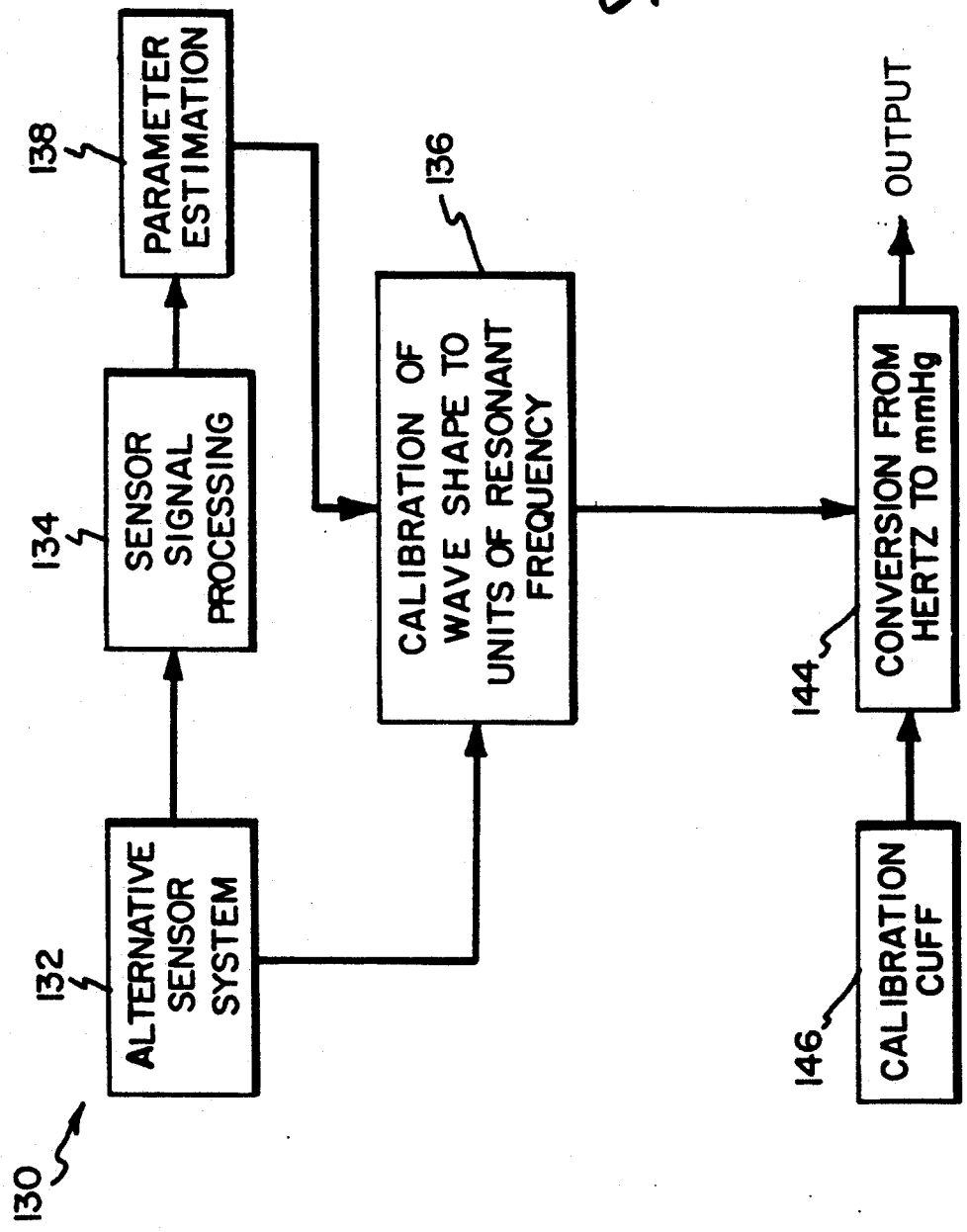
FIG. 20 shows a block diagram of waveform generation and calibration circuitry which uses alternative sensors.

(2) Alternative Means for Obtaining the Time-Varying Arterial Resonant Frequency The method and apparatus for obtaining the time-varying, arterial resonant frequency using parameter estimation methods for the doppler flow velocity signal is described above. Since the time-varying resonant frequency is a parameter of the entire arterial system, other vascular signals may be mathematically characterized to extract the resonant frequency information using parameter estimation techniques similar to those described herein. The examples of alternative sensor systems above may also provide waveshapes possessing information regarding the time-varying resonant frequency of the arterial system. It is necessary that the wave shapes under consideration possess sufficient signal-to-noise ratio and bandwidth to be useful for this purpose. FIG. 20 shows a generalized block diagram 130 for using an alternative sensor system for the waveform generation and an alternative signal for decomposition into the time-varying resonant frequency components.

Diagram 130 shown in FIG. 20 includes an alternative sensor system 132. Alternative sensor system 132 provides signal outputs to sensor signal processing circuit 134 and calibration circuit 136. The output from sensor signal processing circuit 134 is received by a parameter estimation circuit 138. Parameter estimation circuit 138 provides an output to calibration circuit 136. A conversion circuit 144 receives inputs from calibration circuit 136 and a calibration cuff 146. The output from conversion circuit 144 is a calibrated pressure waveform with units of mmHg.

(3) Manifestations of the Time-Varying, Arterial Resonant Frequency on other Arterial Parameters Pressure modulation of the arterial resonant frequency may be indirectly observed by monitoring changes in other arterial parameters. Examples of other parameters that are affected by a change in resonant frequency are:
a) The harmonic time delay of a pressure or flow pulse passing through a resonant arterial segment;
b) The propagation velocity of each harmonic component comprising a pressure or flow pulse within an artery; and
c) The relative amplitude of harmonic components present in the distal segments of arteries.

Figure 21:
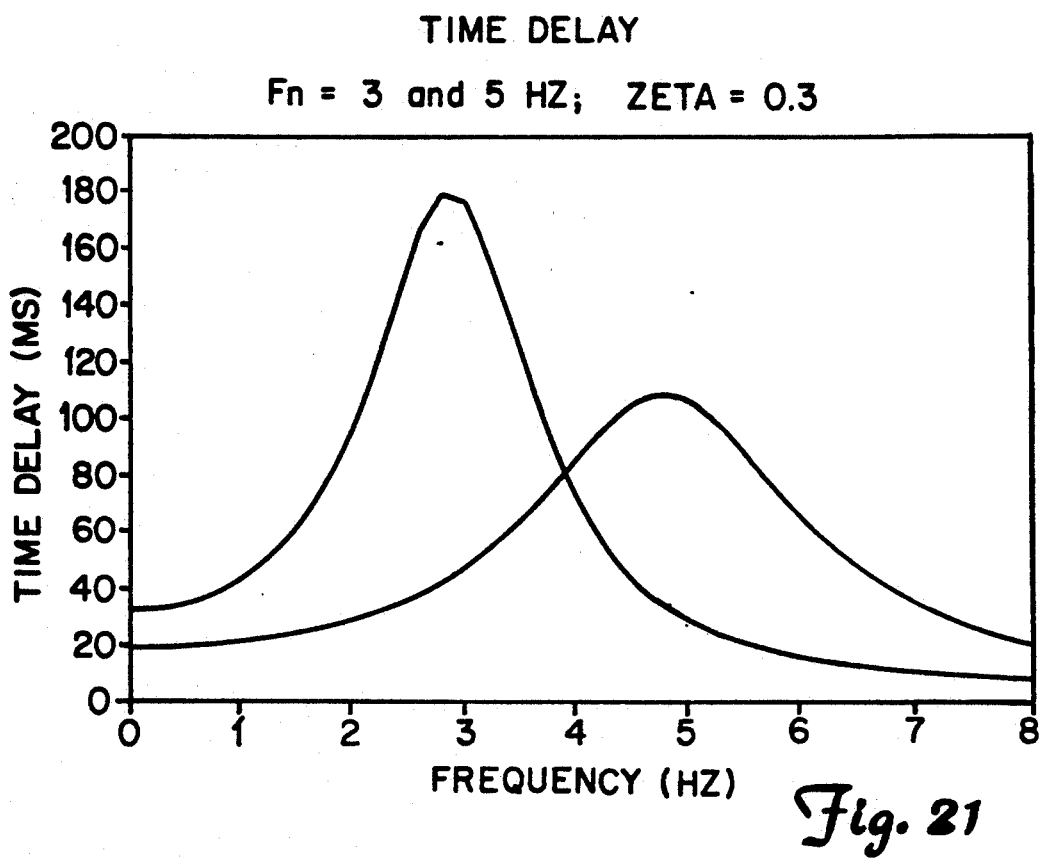
FIG. 21 shows a time delay spectrum for changes in arterial resonant frequency.

The time delay of a signal through any resonant system changes as the resonance of that system changes. This time delay is frequency dependent. FIG. 21 shows the change in time delay for differing frequency components at resonant frequencies of 3 and 5 hertz. (This variable time delay may also be expressed as a variable phase shift.)

Figure 22:
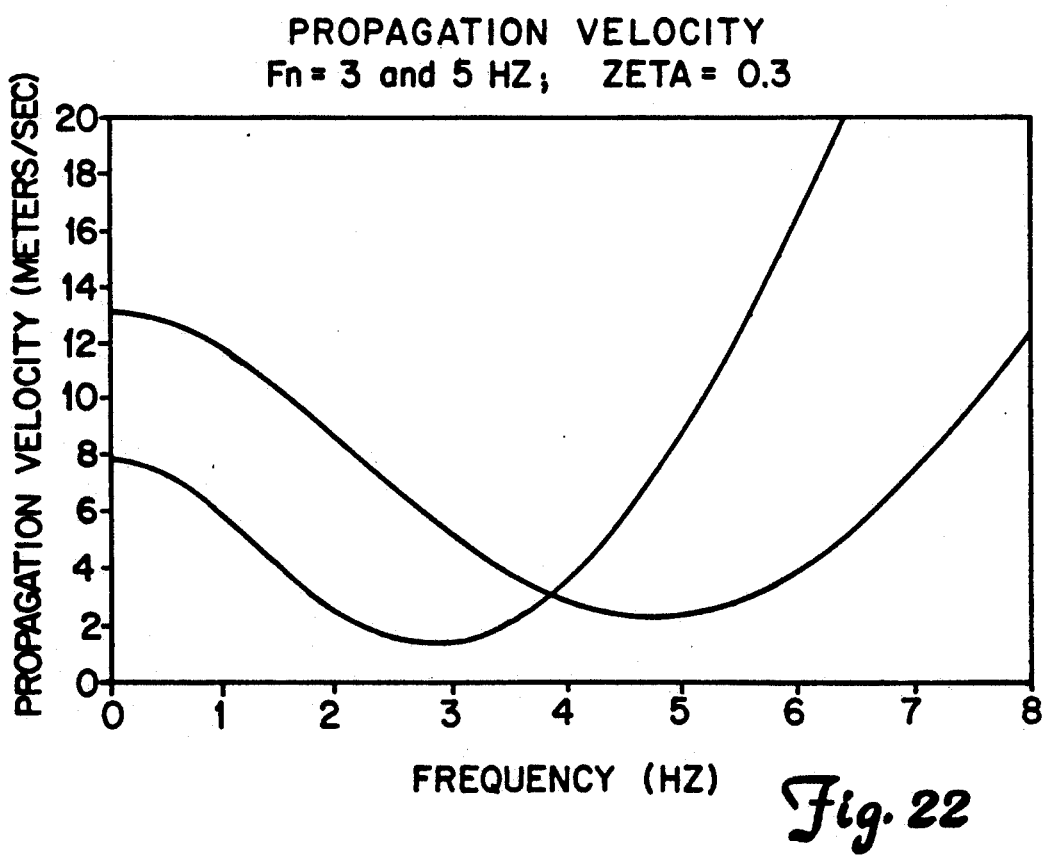
FIG. 22 shows a propagation velocity spectrum for changes in arterial resonant frequency.

The change in time delay described above may be viewed as a change in the propagation velocity of a wave through an arterial segment of fixed length. This propagation velocity may be expressed as:

$$V_p(f) = L/T_d(f) \qquad \text{Equation 39}$$

Where $V_p(f)$ is the propagation velocity as a function of frequency, L is the length of the arterial segment, and $T_d(f)$ is the time delay as a function of frequency. FIG. 22 shows the propagation velocity associated with the resonant frequencies and time delay of FIG. 21 for an arterial segment length of 25 cm.

A resonant system filters the amplitude components of signals passed through it. An arterial segment has this same effect upon the pressure or flow waveforms as they pass through the vessel. The harmonic components closest to the resonant frequency of the vessel exhibit minimal attenuation while those frequencies further from resonance show more significant attenuation.

VI. Conclusion

Although the present invention has been described with reference to preferred embodiments, workers skilled in the art will recognize that changes may be made in form and detail without departing from the spirit and scope of the invention.

What is claimed is:

1. An apparatus for measuring blood pressure comprising:

noninvasive sensor means for providing an output representative of blood flow in a blood carrying artery;

processing circuitry means coupled to the noninvasive sensor means for receiving the output representative of blood flow and providing a processed output;

resonant frequency identification circuitry means coupled to the processing circuitry means for receiving the processed output, calculating a time-varying resonant frequency of the artery and providing a resonant frequency output; and output means coupled to the resonant frequency identification circuitry means for providing an output representative of blood pressure in the artery based upon the resonant frequency output.

2. The apparatus of claim 1 including calibration means coupled to the output means for calibrating a relationship between the time varying resonant frequency of the artery and the blood pressure in the artery.

3. The apparatus of claim 2 wherein the calibration means includes a noninvasive blood pressure measurement cuff.

4. The apparatus of claim wherein the noninvasive sensor means comprises a plurality of doppler sensors.

5. The apparatus of claim 1 wherein the output means includes display means for displaying the output representative of blood pressure in the artery.

6. The apparatus of claim 1 wherein the output representative of blood pressure in the artery comprises a time varying blood pressure waveform.

7. The apparatus of claim 1 including means for receiving the output of blood flow and decomposing the output into representative component parameters representative of a waveform.

8. The apparatus of claim 1 including means for calibrating the resonant frequency output in units of Hertz.

9. The apparatus of claim 1 including means for receiving the resonant frequency output and calculating a waveform corresponding to the time-varying resonant frequency of the artery.

10. An apparatus for measuring blood pressure comprising:

noninvasive blood velocity sensor means for sensing blood flow velocity in an artery;

means, coupled to the noninvasive blood velocity sensor means, for providing an output representative of a resonant frequency of the artery;

a resonant frequency to blood pressure conversion circuit means, coupled to the means for providing an output representative of a resonant frequency of the artery, for converting a resonant frequency of the artery to a blood pressure output; and display means, coupled to the resonant frequency to blood pressure conversion circuit means, for displaying an output representative of blood pressure in the artery.

11. The apparatus of claim 10 including calibration means coupled to the resonant frequency to blood pressure conversion circuit means for calibrating the output representative of blood pressure in the artery.

12. The apparatus of claim 11 wherein the calibration means comprises a noninvasive blood pressure measurement cuff.

13. The apparatus of claim 10 wherein the noninvasive blood velocity sensor means comprises a doppler sensor.

14. The apparatus of claim 10 including means, connected to the noninvasive blood velocity sensor means, for decomposing a blood velocity waveform into its parameter components.

15. The apparatus of claim 10 including means for calibrating the resonant frequency output in units of Hertz.

16. The apparatus of claim 10 including means for receiving the resonant frequency output and calculating a waveform corresponding to the time-varying resonant frequency of the artery.

17. An apparatus for measuring blood pressure comprising:

means for measuring an arterial parameter which correlates to arterial resonant frequency;

means, coupled to the means for measuring an arterial parameter, for calculating blood pressure in the artery based upon arterial resonant frequency; and output means, coupled to the means for calculating blood pressure, for providing an output representative of blood pressure.

18. The apparatus of claim 17 wherein the means for measuring an arterial parameter blood velocity comprises a doppler sensor.

19. The apparatus of claim 17 wherein the means for calculating blood pressure in the artery includes means for determining a resonant frequency waveform of the artery based upon the arterial parameter.

20. The apparatus of claim 17 including processing circuitry coupled to the means for measuring an arterial parameter through an artery.

21. The apparatus of claim 17 including calibration means coupled to the output means for calibrating a relationship between the arterial parameter and blood pressure in the artery.

22. The apparatus of claim 21 wherein the calibration means includes a noninvasive blood pressure measurement cuff.

23. The apparatus of claim 17 wherein the output means includes a display means for displaying the output representative of blood pressure.

24. The apparatus of claim 17 including means, coupled to the means for measuring an arterial parameter for decomposing waveform formed from the arterial parameter into its parameter components.

25. The apparatus of claim 17 including means, coupled to the means for calculating blood pressure, for calibrating arterial resonant frequency output in units of Hertz.

26. The apparatus of claim 17 including means for calculating a waveform corresponding to the time-varying resonant frequency of the artery based upon the blood arterial parameter.

27. A method of testing a blood vessel system, comprising:

deriving from a blood vessel a first signal from which a time-varying resonant frequency is derived;

processing the first signal to produce a second signal representative of the time-varying resonant frequency of the blood vessel system; and providing a test output based upon the second signal representative of the time-varying resonant frequency of the blood vessel system.

28. The method of claim 27 wherein deriving a first signal, comprises deriving from a blood vessel a blood velocity signal representative of blood velocity.

29. The method of claim 27 wherein deriving a first signal, comprises deriving a blood velocity signal from a doppler sensor.

30. The method of claim 27 wherein the output includes a blood pressure output.

31. The method of claim 27 wherein deriving from a first signal comprises, deriving a blood velocity signal based upon doppler shift.

32. A method of measuring blood pressure comprising:
noninvasively deriving from an artery a signal from which time-varying arterial resonant frequency is derived;
processing the signal to produce a waveform representative of time-varying arterial resonant frequency; and
providing a blood pressure output based upon the waveform.

33. The method of claim 32 wherein noninvasively deriving a signal comprises deriving a blood velocity signal.

34. The method of claim 32 wherein processing the signal comprises decomposing the signal into waveform component parameters.

35. The method of claim 32 including calibrating the blood pressure output.

36. A method of blood pressure measurement comprising:
measuring blood flow velocity through an artery;
deriving from the blood flow velocity an arterial resonant frequency waveform; and
providing a blood pressure output based upon the waveform.

37. The method of claim 36 wherein measuring blood flow velocity, comprises measuring doppler shift.

38. The method of claim 36 including calibrating the blood pressure output.

39. A method of measuring blood pressure comprising:
sensing blood flow velocity in an artery with a first noninvasive sensor;
sensing blood flow velocity in the artery with a second noninvasive sensor positioned distally along the artery with respect to the first noninvasive sensor;
deriving from the blood flow velocities sensed by the first and second noninvasive sensors a time-varying arterial resonant frequency waveform; and
providing blood pressure output derived from the waveform.

40. The method of claim 39 wherein sensing blood flow velocities comprises sensing dopper shift.

41. The method of claim 39 including calibrating the blood pressure output.

42. An apparatus for testing a blood vessel system comprising:
a sensor means for coupling to a blood vessel system and providing a sensor output;
means for processing the sensor output to produce a resonant frequency signal representative of a time-varying resonant frequency of the blood vessel system; and
means for providing a test output representative of time-varying resonant frequency of the blood vessel system.

43. The apparatus of claim 42 wherein the sensor means comprises a blood velocity sensor.

44. The apparatus of claim 42 wherein the sensor means comprises a doppler sensor.

45. The apparatus of claim 42 including means for receiving the resonant frequency signal and producing an output representative of blood pressure.

46. The apparatus of claim 42 including means for calibrating an impedance plethysmography sensor to units of resonant frequency based upon the output.

47. The apparatus of claim 42 including means for calibrating an infrared perfusion sensor to units of resonant frequency based upon the output.

48. The apparatus of claim 42 including means for calibrating a partially inflated cuff to units of resonant frequency based upon the output.

49. An apparatus of claim 42 including means for calibrating a pressure transducer for applying against the wall of an artery to units of resonant frequency based upon the output.

50. An apparatus of claim 42 including means for calibrating a radio frequency sensor to units of resonant frequency based upon the output.

51. An apparatus of claim 42 including means for calibrating a magnetic field sensor to units of resonant frequency based upon the output.

52. An apparatus of claim 42 including means for calibrating an ultrasonic sensor to units of resonant frequency based upon the output.

53. An apparatus of claim 42 including means for calibrating changes in arterial geometry to units of resonant frequency based upon the output.

54. The apparatus of claim 42 including means for deriving a nonstationary time delay of components of the output representative of time-varying resonant frequency based upon the output.

55. The apparatus of claim 42 including means for deriving a time-varying propagation velocity of harmonic components of the output representative of a time-varying resonant frequency based upon the output.

56. The apparatus of claim 42 including means for deriving a signal representative of time variable phase shifts in the output representative of a time-varying resonant frequency based upon the output.

57. The apparatus of claim 42 including means for deriving an output representative of pulse-wave velocity based upon the output representative of time-varying resonant frequency based upon the output.

58. An apparatus for measuring blood pressure, comprising:
a noninvasive sensor means for deriving an arterial signal from which time-varying arterial resonant frequency is derived;
signal processing means for receiving the arterial signal and producing an resonant frequency output representative of arterial time-varying resonant frequency; and
means for providing a blood pressure output based upon the resonant frequency output.

59. The apparatus of claim 58 wherein the noninvasive sensor means comprises a blood velocity sensor.

60. The apparatus of claim 58 wherein the signal processing means includes means for decomposing the signal into waveform component parameters.

61. The apparatus of claim 58 including means for calibrating the blood pressure output.

62. An apparatus for measuring blood pressure, comprising:
means for measuring blood flow velocity through an artery;

means for deriving from the blood flow velocity an arterial resonant frequency waveform; and output means for providing a blood pressure output based upon the waveform.

63. The apparatus of claim 62 wherein the means for measuring blood velocity comprises a doppler shift sensor.

64. The apparatus of claim 62 including means for calibrating the blood pressure output.

65. An apparatus for measuring blood pressure comprising:
- a first noninvasive sensor means for sensing blood flow velocity in an artery;
- a second noninvasive sensor means for sensing blood flow velocity in an artery;
- means for deriving from the blood flow velocities sensed by the first and second noninvasive sensor means a time-varying arterial resonant frequency waveform; and
- output means for providing a blood pressure output derived from the waveform.

66. The apparatus of claim 65 wherein the first and second noninvasive sensor means comprise doppler sensors.

67. The apparatus of claim 65 wherein the output means comprises means for providing a blood pressure output representative of blood pressure in the artery.

68. The apparatus of claim 67 including means for calibrating the blood pressure output.

* * * * *

UNITED STATES PATENT AND TRADEMARK OFFICE
CERTIFICATE OF CORRECTION

PATENT NO. : 5,241,964

DATED : September 7, 1993

INVENTOR(S) : GARY L. MCQUILKIN

It is certified that error appears in the above-identified patent and that said Letters Patent is hereby corrected as shown below:

Col. 21, line 25, delete "claim", insert --claim 1--

Signed and Sealed this

Twenty-second Day of March, 1994

Attest:

BRUCE LEHMAN

Attesting Officer

Commissioner of Patents and Trademarks